US011123177B2

(12) United States Patent
Valavanis et al.

(10) Patent No.: US 11,123,177 B2
(45) Date of Patent: Sep. 21, 2021

(54) ADVANCED TENDON GRASPING DEVICES AND DEVICES FOR THEIR APPLICATION

(71) Applicant: TENDOMEND LTD., Nazareth (IL)

(72) Inventors: Stratigoula Valavanis, Kifissia (GR); Ioannis Valavanis, Kifissia (GR)

(73) Assignee: TENDOMEND LTD., Nazareth (IL)

( * ) Notice: Subject to any disclaimer, the term of this patent is extended or adjusted under 35 U.S.C. 154(b) by 232 days.

(21) Appl. No.: 16/540,533

(22) Filed: Aug. 14, 2019

(65) Prior Publication Data

US 2019/0365526 A1 Dec. 5, 2019

Related U.S. Application Data

(63) Continuation of application No. PCT/IB2018/051142, filed on Feb. 23, 2018.

(60) Provisional application No. 62/462,382, filed on Feb. 23, 2017.

(51) Int. Cl.
*A61F 2/08* (2006.01)
*A61B 17/04* (2006.01)
*A61B 17/11* (2006.01)
*A61L 27/36* (2006.01)

(52) U.S. Cl.
CPC ........ *A61F 2/0811* (2013.01); *A61B 17/0401* (2013.01); *A61B 17/1146* (2013.01); *A61L 27/3662* (2013.01); *A61B 2017/0441* (2013.01); *A61F 2002/0823* (2013.01); *A61L 2430/10* (2013.01)

(58) Field of Classification Search
CPC .......... A61F 2/0811; A61F 2002/0823; A61B 17/0401; A61B 17/1146; A61B 2017/0441; A61L 27/3662; A61L 2430/10
See application file for complete search history.

(56) References Cited

U.S. PATENT DOCUMENTS

| | | | |
|---|---|---|---|
| 8,974,470 B2* | 3/2015 | Lampropoulos | A61B 17/32056 606/113 |
| 2001/0004693 A1 | 6/2001 | Burkhead et al. | |
| 2004/0193217 A1 | 9/2004 | Lubbers et al. | |
| 2008/0045881 A1 | 2/2008 | Teitelbaum et al. | |
| 2013/0013065 A1 | 1/2013 | Bills | |
| 2013/0184739 A1 | 7/2013 | Brady et al. | |
| 2014/0277079 A1 | 9/2014 | Vale et al. | |

FOREIGN PATENT DOCUMENTS

WO  WO2012094405  7/2012

* cited by examiner

*Primary Examiner* — George J Ulsh
(74) *Attorney, Agent, or Firm* — Mark David Torche; Patwrite Law

(57) ABSTRACT

Devices used to repair ruptured tendons are described, particularly a tendon grasping device and devices for the application thereof and to the uses if these devices; the tendon grasping device is made of a suitable for surgery bio-compatible material, a series of curved elements connected sequentially to form a hollow deformable structure; in use each curved element surrounds the tendon and the structure deforms between a radially extended condition and a radially retracted condition, in which each curved element firmly surrounds the tendon by applying pressure around the tendon without penetrating it.

10 Claims, 26 Drawing Sheets

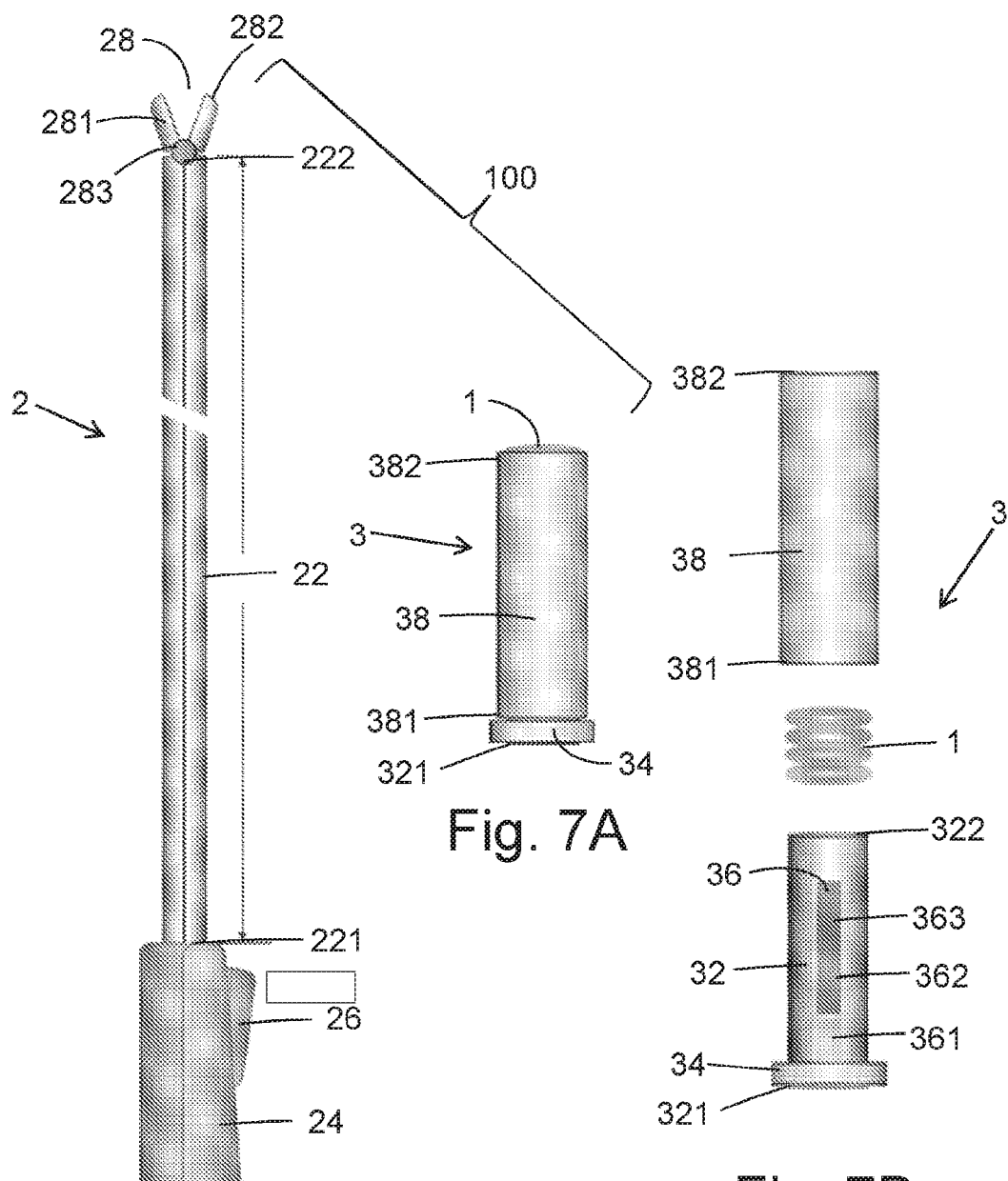

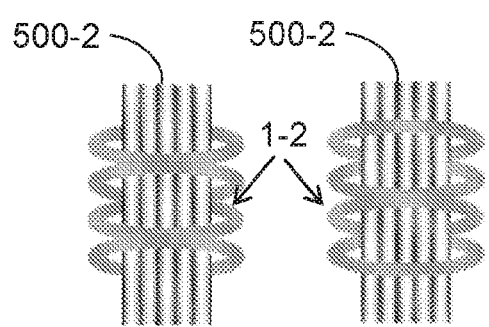
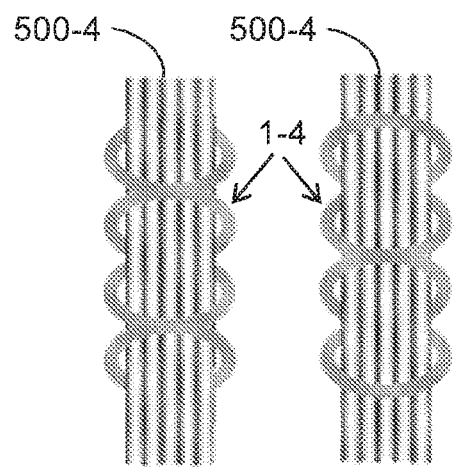
Fig. 15A  Fig. 15B    Fig. 15C  Fig. 15D
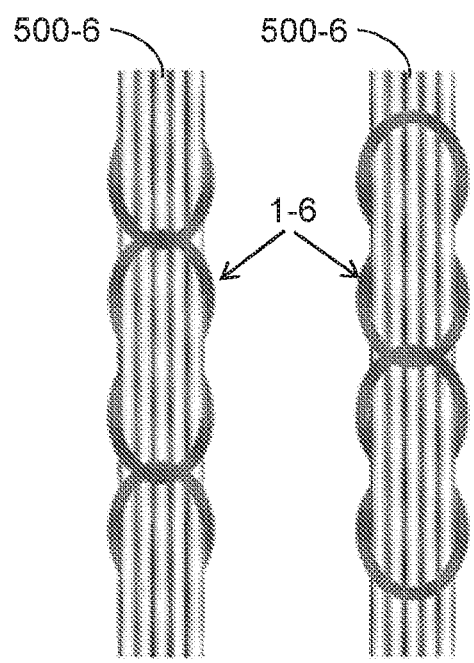
Fig. 15E  Fig. 15F

ADVANCED TENDON GRASPING DEVICES AND DEVICES FOR THEIR APPLICATION

CROSS-REFERENCE TO RELATED APPLICATIONS

The present application is a continuation of international application PCT/IB2018/051142 filed 23 Feb. 2018, which claims priority from U.S. application 62/462,382 filed 23 Feb. 2018, the contents of which is incorporated in its entirety herein by this reference.

TECHNICAL FIELD

The present invention relates to devices that are used to repair ruptured tendons. In particular the invention relates to a tendon grasping device, to a device for the application thereof and to the uses of these devices.

BACKGROUND ART

A tendon is a tough band of fibrous connective tissue that usually connects muscle to bone and is able of withstanding tension. Tendons are subject to injuries, for example due to trauma involving cutting of a tendon, and overuse, generally resulting in inflammation and degeneration of the tendons, which may eventually lead to tendon rupture.

Generally, during a surgical procedure for tendon repair, the torn tendon ends, also known as stumps, are sewed together. If there is not enough healthy tendon to reconnect, a tendon graft is performed, namely implanting a piece of tendon from another part of the body instead of the damaged tendon. In cases of a major tendon rupture, the torn tendon stump is fixed back to the bone.

Devices and methods for surgical procedure for tendon repair are known in the art. For example, United States patent application publication No. 2004/0193217 discloses methods and apparatuses for repairing damaged tendons that include tensile members and anchors configured for insertion within the interior of a tendon. In addition, United States patent application publication No. 2001/0004693 discloses an implant for the fixation of a soft tissue to a bone, including a shaft that penetrates the bone. US2013013065 presents a method for treating damaged tendons or ligaments using a hollow device formed by a woven fabric.

The current surgical techniques for fixing and repairing tendon ruptures involve incomplete initial fixation of the ruptured tendons, need the use of sutures to hold the fixed tissues together, depend on mandatory biological healing of the fixed tissues, require post-operative immobilization for recovery, and allow only gradual mobilization and weight bearing by a treated organ in general, and limb in particular, immediately after the surgical procedure.

SUMMARY OF THE INVENTION

An object of the present invention is to provide a device for treating tendon ruptures, namely reconnecting tendon stumps. A further object of the present invention is to provide a device for treating tendon ruptures involving full initial fixation of the ruptured tendons. A further object of the present invention is to provide a device for treating tendon ruptures that does not need the use of sutures to hold the fixed tissues together. A further object of the present invention is to provide a device for treating tendon ruptures that does not depend on mandatory biological healing of the fixed tissues. A further object of the present invention is to provide a device for treating tendon ruptures that does not require post-operative immobilization for recovery. Yet a further object of the present invention is to provide a device for treating tendon ruptures that allow full mobilization and weight bearing soon after the surgical procedure. A further object of the present invention is a method to use devices of treatment of tendon rupture and a method for treatment of tendon ruptures. A further object of the invention is a device to reduce oedema (swelling) of a tissue, for example a tendon, thus facilitating post-operative sliding movements of the restored tissue.

A tendon grasping device according to the invention is made of a bio compatible material that is suitable for surgery and comprises a series of curved elements that are connected sequentially to form a hollow deformable structure, whereby in use each curved element of the series of curved elements surrounds a tendon and the structure deforms from a radially extended condition to a radially retracted position, in which each curved element firmly surrounds the tendon The curved elements are loops or coils and the series of curved elements includes at least an end loop and a further loop that is connected to the end loop or an end loop and a coil that is connected to the end loop.

When the hollow deformable structure is arranged on a cylindrical surface, either in the radially extended condition or in the radially retracted condition, the cross-sectional area of the deformable structure in the radially retracted condition is smaller than the cross-sectional are of the deformable structure in the radially extended condition—the cross section is normal to the longitudinal axis of the cylindrical surface. When the structure is in the radially extended condition around a tendon, the tendon is in loose state whereas when the structure is in the radially retracted condition around a tendon the tendon is in a squeeze state.

In some embodiments of the invention, when the structure deforms from a radially extended condition to a radially retracted condition, the radius of curvature of at least a portion of a loop or coil that surrounds the tendon is educed. Further, the maximum distance between two points of the structure, i.e. the maximum distance that may be measured between two extreme points of the structure, increases as the tendon grasping device moves from the radially extended condition to the radially retracted condition. In general the structure is extended in the longitudinal direction as it moves from the radially extended condition to the radially retracted condition.

The application of the pressure to the tendon by each individual loop or coil enables the tight grasping of the tendon, once the tendon grasping device is pulled, without damaging the tendon. By connecting the sequentially arranged curved element, i.e. loops or coils, once a pulling force is applied to an end loop or coil, the pulling force is transmitted to all loops or coils, so that each loop or coil in the sequentially arranged loops or coils, is tightly fitted around the tendon.

Preferably the tendon grasping device comprises a continuous linear element, such as a thread or a ring, with portions of the linear element being connected at connecting points to form a series of sequentially flexibly connected loops. The connection of the portions of the linear element at the connecting points may be effected by one of the following: a) intercrossing the linear portions, b) knots, c) discrete connectors.

In an embodiment of the invention the tendon grasping device comprises a series of loops that are connected sequentially and having a zigzag lateral profile, which profile has a series of sequential legs When the tendon grasping device moves from/to a radially extended condition to/from a radially retracted condition, at least an angle that is formed between two sequential legs varies.

In another embodiment of the invention the tendon grasping device comprises a series of loops, which is flexibly connected with either one or maximum two other loops at connecting points. Optionally, one or more loops in the series of loops is formed by a discrete ring. In another embodiment the tendon grasping device is a helical spring.

The tendon grasping device may have attachment means to attach the tendon grasping device to a second tendon grasping device. These means that preferably are directly attached to a loop or coil of the structure comprises at least one or more of the following: a) suture thread, b) clip, c) resilient ratchet element.

In some embodiments the tendon grasping device is made at least partially from bio-degradable material. Examples of materials that may be used to manufacture the tendon grasping device, at least partially, includes: nitinol, suture strings, bio-compatible fibers or any combination thereof.

The tendon grasping device may be arranged in the radially extended condition around a sleeve. Such a device may be preferably from a material with shape memory, so that when the tendon grasping device is removed from the sleeve, it is retracted to the radially retracted condition by resilient forces. Such a device may be also attached to a further structure with at least one loop that is made from a different material, in particular a material with no resilience. A pusher, for example a handle or a further sleeve or a further sleeve with a handle or any other suitable element, may be mounted around the sleeve and is slidable along the sleeve, to push and release the tendon grasping device from the sleeve. The sleeve that is surrounded from the tendon grasping device may be hollow and may slide on an either rigid or deformable stem. A deformable and flexible stem facilitates to guide the tendon grasping device through the body tissues. In one embodiment there is a tool to guide the tendon grasping device, whereby the tool is like a pair of scissors with two elongated elements pivotably connected. The stem may be attached to the first elongated element and the stem may be attached to a second elongated element.

Several tendon grasping devices of different sizes may include in a kit.

An injured tendon and preferably the tendon grasping device may be covered by a tendon cover to protect the injured tendon. Such a cover, which is like a finger glove, may be used without a tendon grasping device, it minimizes tissue oedema and facilitate sliding movement of the restored tendon.

According to the invention there is a cartridge for a tendon grasping device. The cartridge includes a hollow external cylinder, an internal cylinder movable telescopically within the external cylinder, first connecting means on the internal cylinder to releasably connect a tendon grasping device to the internal cylinder and second connecting means on the external cylinder to releasably connect a tendon grasping device to the external cylinder.

The internal cylinder may have a leading edge that penetrates the external cylinder through a first opening of the external cylinder, with the leading edge being within the external cylinder when the internal cylinder moves within the external cylinder. The external cylinder has a second opening opposite the first opening. The tendon grasping device extends between the leading edge and the second opening and beyond the leading edge of the internal cylinder so that the hollow deformable structure remains free to receive and surround the tendon. The internal cylinder may have a following edge with a stopper that prohibits the following edge to enter the hollow external cylinder.

According to the invention there is an applicator for a tendon grasping device. The applicator is rigid or deformable and receives a cartridge carrying a tendon grasping device. Further, the applicator has means at one end of the stem configured to releasably grip an end of a tendon stump, whereby when the cartridge is on the stem, the cartridge is movable along the stem and passing the gripper means with one end thereof, is configured to release the tendon grasping device from the applicator. The applicator may comprise a handle at a distance from the gripper means, which includes operating means to operate the gripper means.

A method to grasp a tendon with a tendon grasping device according to the invention includes i) surrounding the tendon with at least one loop and ii) tightening the tendon grasping device lengthwise, so that the tendon grasping device moves from a radially extended condition to a radially retracted position to grasp the tendon, whereby the grasping of the of the tendon is effected by contact forces developed between the surface of the tendon and the at least one loop, preferably the two loops, without penetrating the tendon. The method may include placing a tubular tendon cover tightly around the tendon and the tendon grasping device. Tightening of the tendon grasping device to grasp the tendon, may be effected by applying a tension action lengthwise to the tendon grasping device.

BRIEF DESCRIPTION OF THE DRAWINGS

Embodiments are described below, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice:

FIG. 6 schematically illustrates, according to an exemplary embodiment, a lateral view of a body of an applicator.

FIGS. 7A and 7B schematically illustrate, according to an exemplary embodiment, a lateral view and an exploded lateral view, respectively, of a cartridge.

FIGS. 15A-F summarize the three major states of grasping a tendon with a tendon grasping device.

DETAILED DESCRIPTION OF THE INVENTION

Figure 1A:
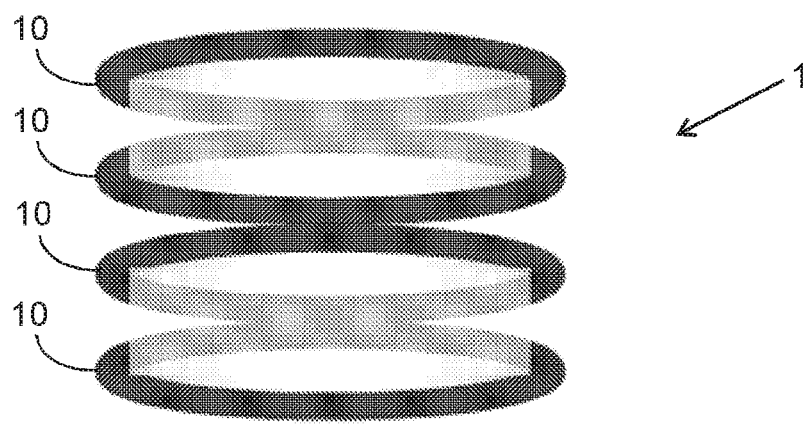
FIGS. 1A and 1B schematically illustrate, according to an exemplary embodiment, an anteroposterior and lateral view, respectively, of a tendon grasping device.

Before explaining at least one embodiment in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale. Some non-essential elements may have been omitted from some of the drawings.

Figure 1B:
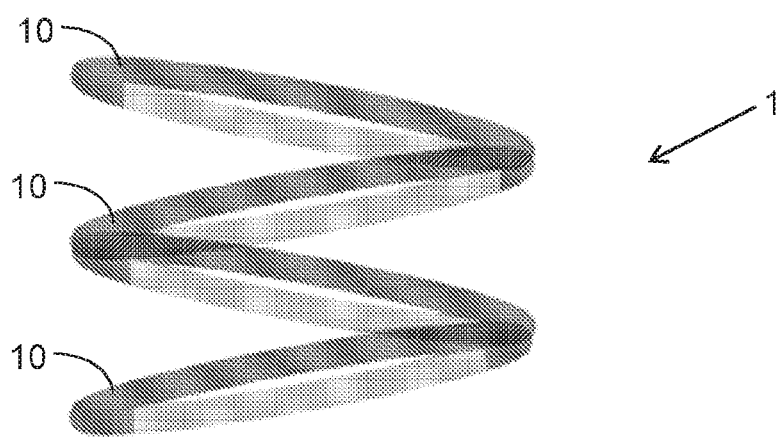

FIGS. 1A and 1B schematically illustrate, according to an exemplary embodiment, an anteroposterior and lateral view, respectively, of a tendon grasping device 1, configured to grasp a tendon stump. The tendon grasping device 1 comprises a series of a plurality of curved elements, in the embodiment of the Figs the curved elements are the loops 10, made of a thread and arranged sequentially, i.e. successively arranged and connected one after the other, in a flexible and deformable hollow tubular-like disposition to form a tubular-like structure, such as a cylinder-like structure having a first end and a second end. Such a structure may have any cross-section, for example a circular cross-section or an elliptical cross-section. The hollow structure is made of flexible material, so that the loops are deformable. In contrast to prior art devices, which are inserted into the tendon tissue in order to anchor a tendon stump to another tendon stump or to a bone, the tendon grasping device 1 of the present invention surrounds and tightly grasps the tendon, thus eliminating the damage that might be caused to the tendon tissue following the usage of prior art devices. A loop is a structural element of the tendon grasping device 1 extending along a path that crosses itself. Crossing may be effected by various ways, for example by intercrossing, using a connector, tying a knot, using a ring etc.

Alternatively the tendon grasping device may comprise a series of coils that are arranged sequentially in a flexible hollow tubular-like structure having a first end and a second end. A coil is a structural element of the tendon grasping device 1 extending along a full turn of a helical path. A loop at one end of the coil facilitates the attachment of the coil to the tendon. The coil may be provided with loops at its two ends.

The tendon grasping device 1 is made of any material known in the art suitable for surgery-compatible threads. According to one embodiment, the tendon grasping device 1 is made of a biocompatible material, for example biocompatible fibers. According to another embodiment, the tendon grasping device 1 is made of an absorbable (bio-degradable) biocompatible material. According to yet another embodiment, the tendon grasping device 1 is made of a non-absorbable biocompatible material. According to a preferred embodiment, the tendon grasping device 1 is made of any suture thread material or suture string material known in the art, for example a biological material like silk; a synthetic absorbable (bio-degradable) material like poly glycolic acid, polylactic acid, monoacryl and polydioxanose; and a synthetic non-absorbable material like nylon, polyester, polyvinylidene difluoride and polypropylene. According to another preferred embodiment the tendon grasping device 1 is made at least partially from nitinol, i.e. nickel titanium or any other biocompatible alloy.

Figure 2A:
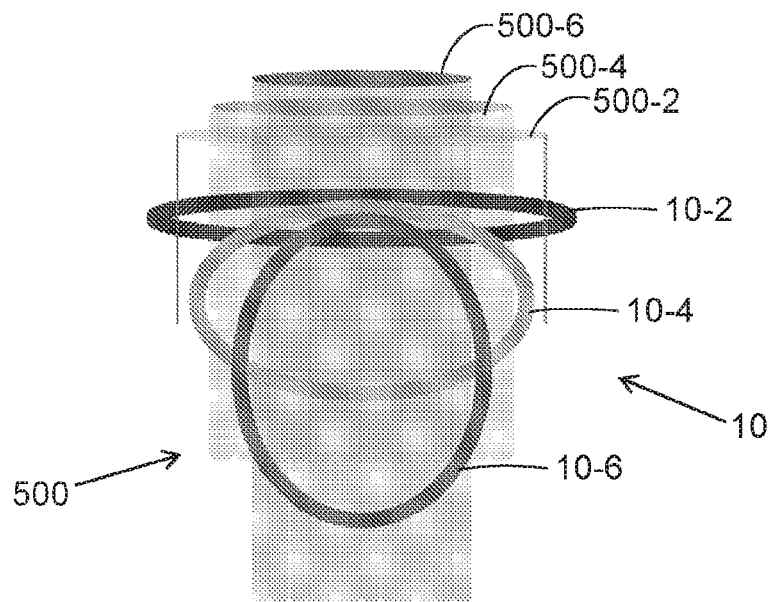
FIGS. 2A and 2B schematically illustrate, according to an exemplary embodiment, an anteroposterior and lateral view, respectively, of three major states of a loop of a tendon grasping device relative to a tendon grasped by the loop.
Figure 2B:
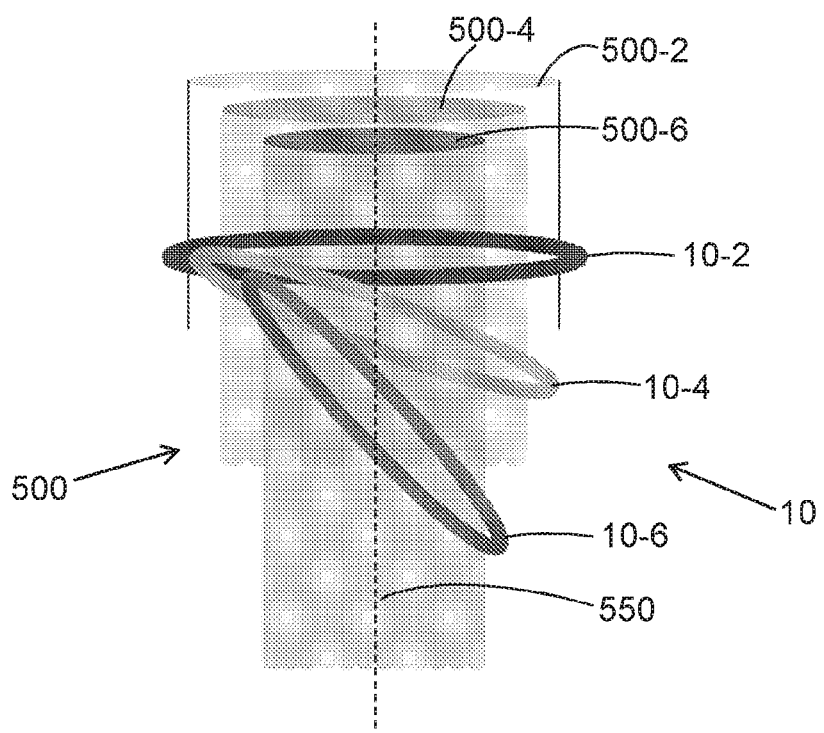

Each loop 10 of the tendon grasping device 1 may be in three major states relative to a tendon grasped by the loop 10. FIGS. 2A and 2B schematically illustrate, according to an exemplary embodiment, an anteroposterior and lateral view, respectively, of three major states of a loop 10 of a tendon grasping device 1 relative to a tendon 500 grasped by the loop 10. The loop 10 assumes the three major states following stretching or loosening of the tendon grasping device 1. According to one embodiment, the three major states of the loop 10 are: loose loop 10-2, contacting loop 10-4 and squeezing loop 10-6. As a result, the tendon 500 assumes three major respective states: loose tendon 500-2, contacted tendon 500-4 and squeezed tendon 500-6. The loose loop 10-2 surrounds a loose tendon 500-2 while keeping a gap between the loose loop 10-2 and the loose tendon 500-2. At the loose state the normal structure of the loop 500 is not affected. Upon stretching of the tendon grasping device 1 to a certain extent, the loop 10 assumes the state of contacting loop 10-4 and as a result the tendon 500 assumes the state of contacted tendon 500-4. At the contact state, the contacting loop 10-4 is in contact with the contacted tendon 500-4 and there is a slight distraction of the contacted tendon 500-4 due to a slight pressure exerted on the contacted tendon 500-4 by the contacting loop 10-4. Upon further stretching of the tendon grasping device 1, the loop 10 assumes the state of squeezing loop 10-6 and as a result the tendon 500 assumes the state of squeezed tendon 500-6. At the squeeze state, the squeezing loop 10-6 is in contact with the tendon 500 at individual points arranged in a non-uniform disposition around a cross-section of the tendon 500-6—a cross-section of the tendon is normal to its longitudinal axis 550—and along a line that crosses the cross-section. In such a state the squeezing loop 10-6 squeezes the squeezed tendon 500-6 and due to a pressure exerted on the squeezed tendon 500-6 to a large extent by the squeezing loop 10-6, there is a deformation of the squeezed tendon 500-6, namely the squeezed tendon 500-6 is more constricted in comparison to the loose tendon 500-2 and the contacted tendon 500-4.

FIG. 2B clearly illustrates other embodiments relating to an angle between the loop 10 and the longitudinal axis 550 of the tendon 500 in the three major states. According to one embodiment, in the loose state, the angle between the loose loop 10-2 and the longitudinal axis 550 of the loose tendon 500-2 is substantially perpendicular. According to another embodiment, the angle between the loose loop 10-2 and the longitudinal axis 550 of the loose tendon 500-2 may be less than substantially 90 degrees, depending on the extent of loosening of the tendon grasping device 1 (not shown). According to yet another embodiment, the angle between the contacting loop 10-4 and the longitudinal axis 550 of the contacted tendon 500-4 is smaller than the angle between the loose loop 10-2 and the longitudinal axis 550 of the loose tendon 500-2. According to still another embodiment, the angle between the squeezing loop 10-6 and the longitudinal axis 550 of the squeezed tendon 500-6 is smaller than the angle between the contacting loop 10-4 and the longitudinal axis 550 of the contacted tendon 500-4.

FIGS. 3A-3D schematically illustrate a tendon 500 grasped by a tendon grasping device 1 in the three major states: loose tendon grasping device 1-2, contacting tendon grasping device 1-4 and squeezing tendon grasping device 1-6.

A lateral view of the embodiment of the tendon grasping device 1 of FIG. 2B has a zigzag pattern, with the angle between two successive loops 10 varying as the tendon grasping device 1 moves from retracted condition, i.e. loose tendon grasping device 1-2 to the extended condition, i.e. contacting tendon grasping device 1-4 or squeezing tendon grasping device 1-3.

Figures 3A, 3B:
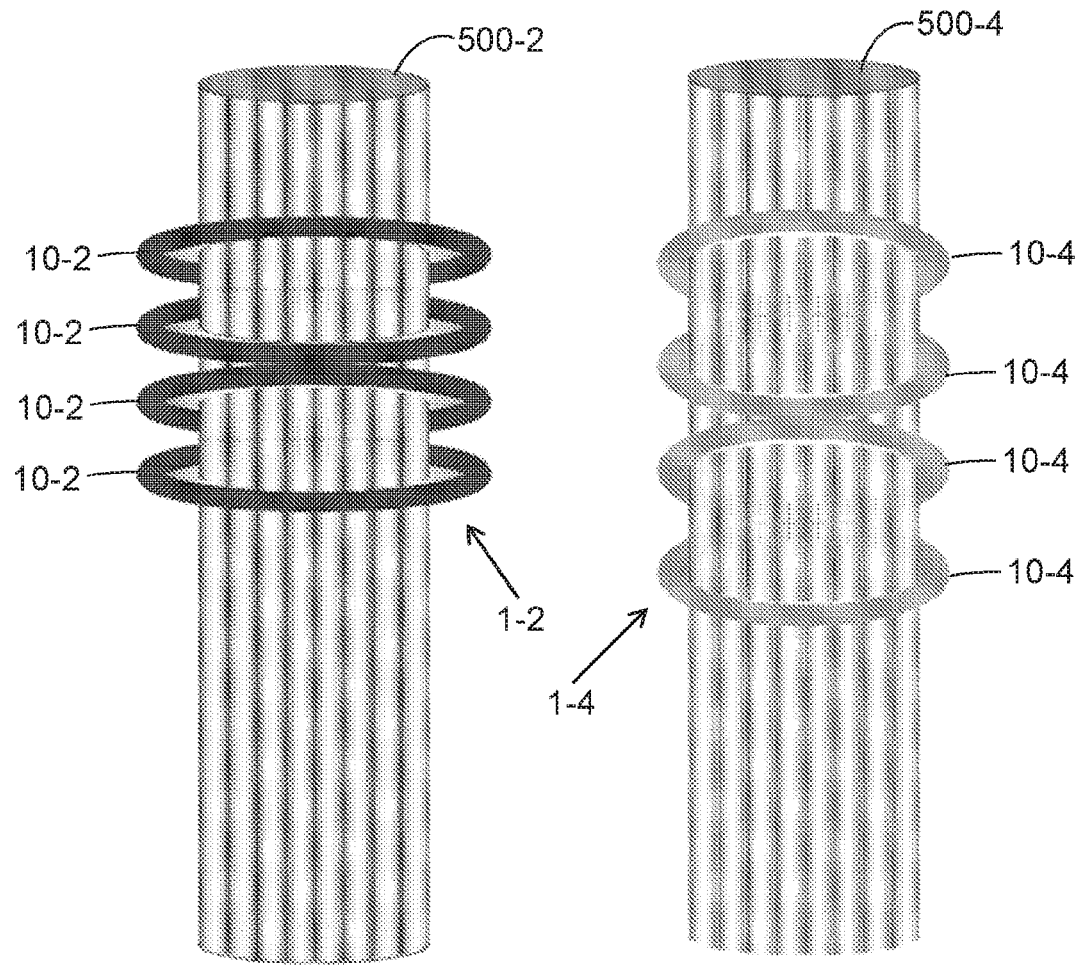
FIGS. 3A to 3D schematically illustrate a tendon grasped by a tendon grasping device in three major states: loose tendon grasping device, contacting tendon grasping device and squeezing tendon grasping device.

FIG. 3A schematically illustrates, according to an exemplary embodiment, an anteroposterior view of a loose tendon 500-2 inserted into a hollow cylinder like structure defined by a loose tendon grasping device 1-2. At this loose state, there is a gap between the loose loops 10-2 of the tendon grasping device 1-2 and the loose tendon 500-2. Thus, a loose tendon 500-2 may be freely inserted into the hollow cylinder-like structure of the loose tendon grasping device 1-2, allowing easy positioning of the loose tendon grasping device 1-2 along the loose tendon 500-2.

Then, the loose tendon grasping device 1-2 is stretched until the loops 10 come in contact with the tendon 500.

In general, the tendon grasping device 1 deforms between a radially extended condition, with the curved elements, i.e. the loop(s) or/and coil(s), being loose or partially loose around tendon 500 and a radially retracted condition, with the curved elements, tightly grasping the tendon 500. The radial direction is the direction normal to the axis 550 of the tendon, when the tendon grasping device 1 surrounds a tendon 500, or normal to the longitudinal direction of the tendon grasping device 1. The longitudinal direction of the tendon grasping device 1 coincides with the direction of arrow 932 or arrow 930 of FIGS. 12A to 12C.

FIG. 3B schematically illustrates, according to an exemplary embodiment, an anteroposterior view of a contacted tendon 500-4 being in contact with a contacting tendon grasping device 1-4. At the contact state, the contacted tendon 500-4 is slightly distracted due to a slight pressure exerted on the contacted tendon 500-4 by the contacting loops 10-4 of the contacting tendon grasping device 1-4.

Then, the contacting tendon grasping device 1-4 is stretched until the loops squeeze the tendon 500.

Figure 3C:
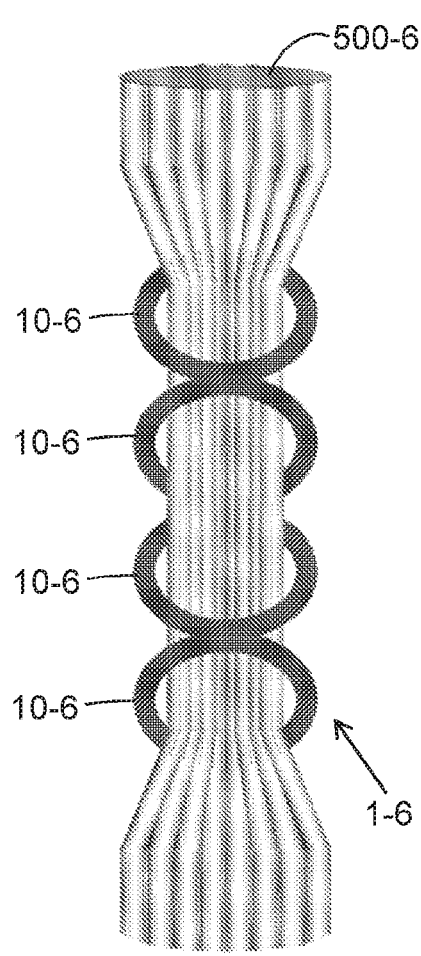
Figure 3D:
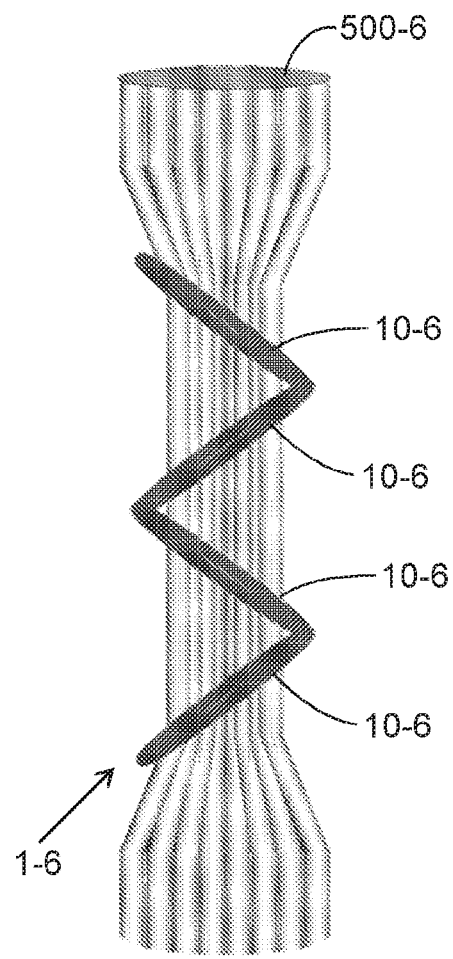

FIGS. 3C and 3D schematically illustrate, according to some exemplary embodiments, an anteroposterior view and a lateral view, respectively, of a squeezed tendon 500-6 being squeezed by a squeezing tendon grasping device 1-6. At the squeeze state, due to a pressure exerted on the squeezed tendon 500-6 to a large extent by the squeezing loops 10-6 of the squeezing tendon grasping device 1-6 there is a deformation of the squeezed tendon 500-6, namely the site of the squeezed tendon 500-6 squeezed by the squeezing tendon grasping device 1-6 is constricted. At the squeeze state, the squeezing tendon grasping device 1-6 tightly grasps the squeezed tendon 500-6.

According to some embodiments, the tendon grasping device 1 is made of a linear element, such as a thread or a string, with portions of the linear element being connected or intercrossed at the connecting points to form a sequence of loops 10. According to some embodiments, the tendon grasping device 1 is made of a thread knotted to form a sequence of a plurality of loops 10. The thread may be knotted in various ways: simple crossing, intercrossing, knot-like intercrossing, connector-aided intercrossing, and any combination thereof. A tendon grasping device according to the invention, with two loops provides a firm tightening of the tendon.

Figure 4A:
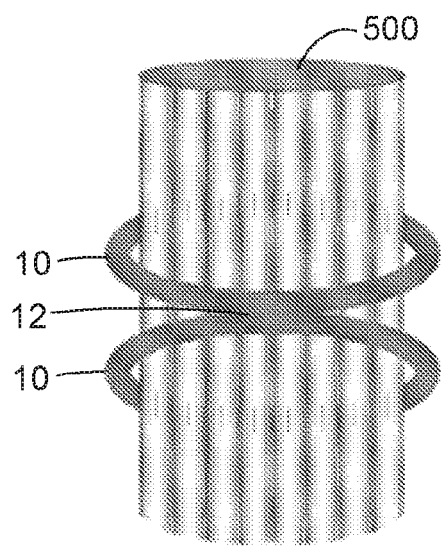
FIG. 4A schematically illustrates, according to an exemplary embodiment, an anteroposterior view of two loops of a tendon grasping devices made by simple crossing of a thread, without changing the direction of the thread.

FIG. 4A schematically illustrates, according to an exemplary embodiment, an anteroposterior view of two loops 10 of a tendon grasping devices 1 made by simple crossing 12 of a thread, without changing the direction of the thread.

Figure 4B:
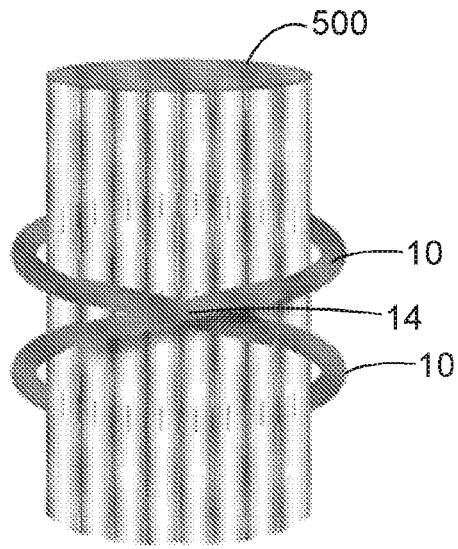
FIG. 4B schematically illustrates, according to an exemplary embodiment, an anteroposterior view of two loops of a tendon grasping devices made by intercrossing of a thread.

FIG. 4B schematically illustrates, according to an exemplary embodiment, an anteroposterior view of two loops 10 of a tendon grasping devices 1 made by intercrossing 14 of a thread. According to one embodiment, the thread is intercrossed 14 at one side of a hollow cylinder-like structure defined by the tendon grasping device 1, as illustrated in FIG. 4B, without changing the direction of the thread. According to another embodiment, the thread is intercrossed 14 at one side of the hollow cylinder-like structure defined by the tendon grasping device 1, with changing the direction of the thread (not shown). According to yet another embodiment, when the tendon grasping device 1 comprises more than two loops 10, the thread is intercrossed 14 at two sides of the hollow cylinder-like structure defined by the tendon grasping device 1, without changing the direction of the thread (not shown). According to still another embodiment, when the tendon grasping device 1 comprises more than two loops 10, the thread in intercrossed 14 at two sides of the hollow cylinder like structure defined by the tendon grasping device 1, with changing the direction of the thread (not shown).

Figure 4C:
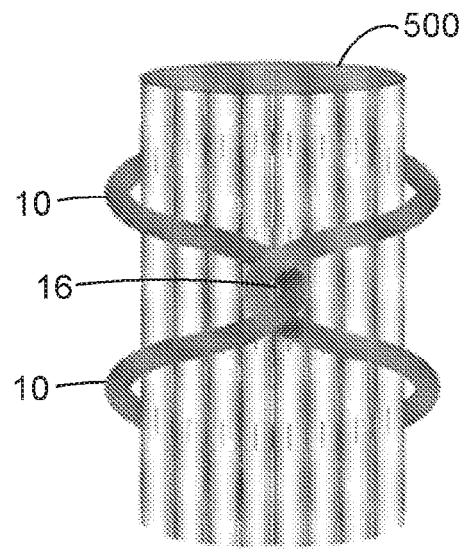
FIG. 4C schematically illustrates, according to an exemplary embodiment, an anteroposterior view of two loops of a tendon grasping devices made by knot-like intercrossing of a thread.

FIG. 4C schematically illustrates, according to an exemplary embodiment, an anteroposterior view of two loops 10 of a tendon grasping devices 1 made by knot-like intercrossing 16 of a thread. According to one embodiment, the thread is knot-like intercrossed 16 at one side of a hollow cylinder-like structure defined by the tendon grasping device 1, as illustrated in FIG. 4C, without changing the direction of the thread, According to another embodiment, the thread is knot-like intercrossed 16 at one side of the hollow cylinder-like structure defined by the tendon grasping device 1, with changing the direction of the thread (not shown). According to yet another embodiment, when the tendon grasping device 1 comprises more than two loops 10, the thread is knot-like intercrossed 16 at two sides of the hollow cylinder-like structure defined by the tendon grasping device 1, without changing the direction of the thread (not shown). According to still another embodiment, when the tendon grasping device 1 comprises more than two loops 10, the thread in knot-like intercrossed 16 at two sides of the hollow cylinder-like structure defined by the tendon grasping device 1, with changing the direction of the thread (not shown).

Figure 4D:
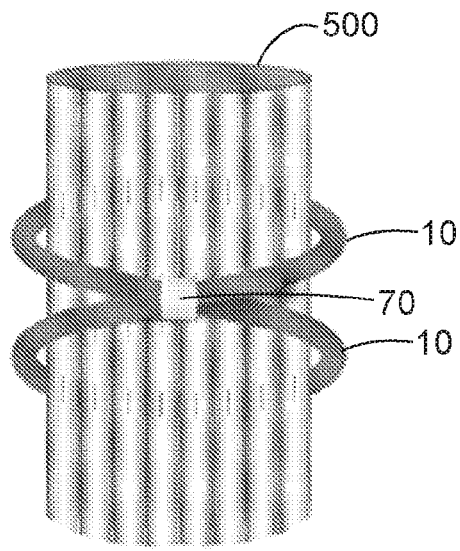
FIG. 4D schematically illustrates, according to an exemplary embodiment, an anteroposterior view of two loops of a tendon grasping devices made by connector-aided intercrossing of a thread.

FIG. 4D schematically illustrates, according to an exemplary embodiment, an anteroposterior view of two loops 10 of a tendon grasping devices 1 made by connector 70-aided intercrossing 16 of a thread. According to some embodiments, the connector 70 is configured to connect two loops 10 of a tendon grasping device 1. The discrete connector 70 may be made of any material, and be in any structure, known in the art making it suitable for connecting two loops of a tendon grasping device. Examples of a connector 70 include, but not limited two, a thread configured to tie two loops 10 together, a ring like connector 70 made of a rigid or flexible material, like metal or plastic, and the like.

According to the embodiment illustrated in FIG. 4D, the thread is connector 70-aided intercrossed at one side of a hollow cylinder-like structure defined by the tendon grasping device 1, without changing the direction of the thread. According to another embodiment, the thread is connector 70-aided intercrossed at one side of the hollow cylinder-like structure defined by the tendon grasping device 1, with changing the direction of the thread (not shown), According to yet another embodiment, when the tendon grasping device 1 comprises more than two loops 10, the thread is connector 70-aided intercrossed at two sides of the hollow cylinder-like structure defined by the tendon grasping device 1, without changing the direction of the thread (not shown). According to still another embodiment, when the tendon grasping device 1 comprises more than two loops 10, the thread in connector 70-aided intercrossed at two sides of the hollow cylinder-like structure defined by the tendon grasping device 1, with changing the direction of the thread (not shown).

According to one embodiment, the number of loops 10 in a tendon grasping device 1 depends on the size of the tendon 500 to be grasped. According to another embodiment, the number of loops 10 in a tendon grasping device 1 depends on the strength of the tendon 500 to be grasped. According to yet another embodiment, the number of loops 10 in a tendon grasping device 1 depends on the size and strength of the tendon 500 to be grasped. According to a further embodiment, the number of loops 10 in a tendon grasping device 1 depends on the extent of damage caused to the tendon 500 to be grasped. According to an additional embodiment, the number of loops 10 in a tendon grasping device 1 depends on any combination of the aforementioned factors.

According to one embodiment, the thickness of the thread of which the tendon grasping device 1 is made depends on the material of which the thread is made. According to another embodiment, the thickness of the thread of which the tendon grasping device 1 is made depends on the size of the tendon 500 to be grasped.

According to yet another embodiment, the thickness of the thread of which the tendon grasping device 1 is made depends on the strength of the tendon 500 to be grasped. According to a further embodiment, the thickness of the thread of which the tendon grasping device 1 is made depends on any combination of the aforementioned factors.

According to one embodiment, the length and diameter of the cylinder like structure defined by the tendon grasping device 1 are reversibly changeable due to the flexibility of the sequence of the plurality of loops 10. When the tendon grasping device 1 is fully longitudinally compressed, the diameter of the tendon grasping device 1 is maximal, and when the tendon grasping device 1 is fully longitudinally elongated, the diameter of the tendon grasping device 1 is minimal. Thus, in order to increase the diameter of the tendon grasping device 1 the tendon grasping device 1 is longitudinally compressed, and in order to decrease the diameter of the tendon grasping device 1 the tendon grasping device 1 is longitudinally extended. In addition, the length of the cylinder-like structure defined by the tendon grasping device 1 is determined by the number of loops 10 comprising the tendon grasping device 1. As the number of loops 10 increases, the length of the tendon grasping device 1 increases as well.

According to some embodiments, the tendon grasping device 1 is configured to facilitate reconnection of two tendon stumps of a ruptured tendon 500. According to one embodiment, the two tendon stumps are grasped by a tendon grasping device 1. According to another embodiment, each tendon stump is grasped by a tendon grasping device 1, and the two tendon grasping devices are connected to each other.

Figures 5A, 5B:
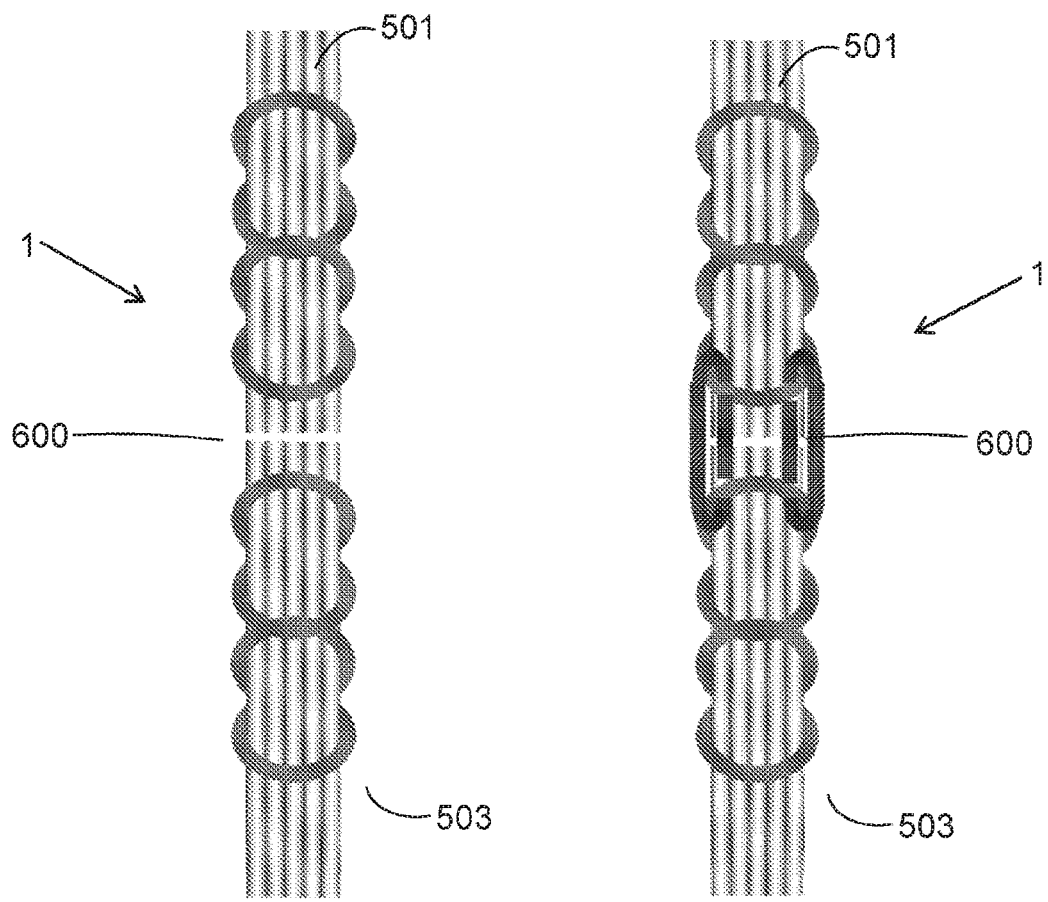
FIGS. 5A and 5B schematically illustrate, according to an exemplary embodiment, an anteroposterior view and a lateral view, respectively, of a first tendon stump reconnected with a second tendon stump by using a tendon grasping device.

FIGS. 5A and 5B schematically illustrate, according to an exemplary embodiment, an anteroposterior view and a lateral view, respectively, of a first tendon stump 501 reconnected with a second tendon stump 503 by using a tendon grasping device 1. The tendon grasping device 1 is configured to grasp both the first tendon stump 501 and the second tendon stump 503, when an end of the first tendon stump 501 is held in close proximity to an end of the second tendon stump 503, until the first tendon stump 501 knits with the second tendon stump 503, and the gap 600 between the two tendon ends is enclosed, to form a healed tendon 500.

FIGS. 6 and 7A schematically illustrate, according to an exemplary embodiment, a lateral view of the main components of an applicator of a tendon grasping device, designated hereinafter as "applicator 100". The applicator 100 comprises a body 2 and a cartridge 3.

FIG. 6 schematically illustrates, according to an exemplary embodiment, a lateral view of a body 2 of an applicator 100. The body 2 comprises a stem 22 having a first end 221 and a second end 222. According to one embodiment, the stem 22 is telescopic and is made accordingly as known in the art, for example by having sections that slide inside one another. Thus, it is possible to extend or shorten the stem 22 as desired. A handle 24, configured to be held by a user, is attached to the first end 221 of the stem 22, and a gripper 28, configured to grip a tendon or an end of a tendon stump, is attached to the second end 222 of the stem 22. Any type of gripper 28 known in the art is under the scope of the present invention. According to a preferred embodiment, illustrated in FIG. 6, the gripper 28 comprises a first jaw 281 axially connected with an axis 283 to a second jaw 282. Additional embodiments of the gripper 28 and its mode of action will be described later. According to another preferred embodiment, the handle 24 further comprises a button 26, configured to actuate the gripper 28. According to one embodiment, the button 26 is physically connected to the gripper 28, for example but not limited to, with a cable (not shown) or a shaft (not shown) extended through the stem 22. According to another embodiment, the button 26 may be connected to the gripper 28 by any other mechanism known in the art, for example but not limited to, wireless communication and the like.

FIGS. 7A and 7B schematically illustrate, according to an exemplary embodiment, a lateral view and an exploded lateral view, respectively, of a cartridge 3. According to the embodiment illustrated in FIG. 7B, the cartridge 3 comprises an internal cylinder 32 and an external cylinder 38, wherein the external cylinder 38 is configured to accommodate in its inner space the internal cylinder 32 and a tendon grasping device 1 placed in continuation to the internal cylinder 32, i.e. extending beyond an end base of the internal cylinder 32. The internal cylinder 32 comprises a first edge 32, i.e. a leading edge, and a second edge 322, i.e. a following edge, and the external cylinder 38 comprises a first opening 381 and a second opening 382. According to another embodiment, the internal cylinder 32 further comprises a stopper 34 having a ring-like structure attached substantially near the first edge 321. When a tendon grasping device 1 is pushed into the external cylinder 38 for example through its first opening 381, followed by the internal cylinder 32 with the second edge 322 forward, the stopper 34 is configured to engage with the wall of the first opening 381 of the external cylinder 38 and prevent further insertion of the internal cylinder 32 into the external cylinder 38.

FIG. 7A schematically illustrates an assembled cartridge 3, comprising a tendon grasping device 1 and an internal cylinder 32 inserted into the external cylinder 38. The edge of the tendon grasping device 1 is seen extending from the second opening 382 of the external cylinder 38, and the internal cylinder 32 is fully inserted into the external cylinder 38, when the stopper 34 engages with the wall of the first opening 381 of the external cylinder 38.

According to yet another embodiment, the internal cylinder 32 further comprises an index 36. According to a preferred embodiment, the index 36 comprises three markings: a first marking 361 positioned proximally to the first edge 321 of the internal cylinder 32—designating "full compression of the tendon grasping device 1"; a second marking 362 positioned further distally to the first edge 321—designating "mild extension of the tendon grasping device 1"; and a third marking 363 positioned most distally to the first edge 321—designating "full extension of the tendon grasping device 1". Embodiments of the usage of the index 36 will be understood by reference to the following figures.

Figures 8A, 8B:
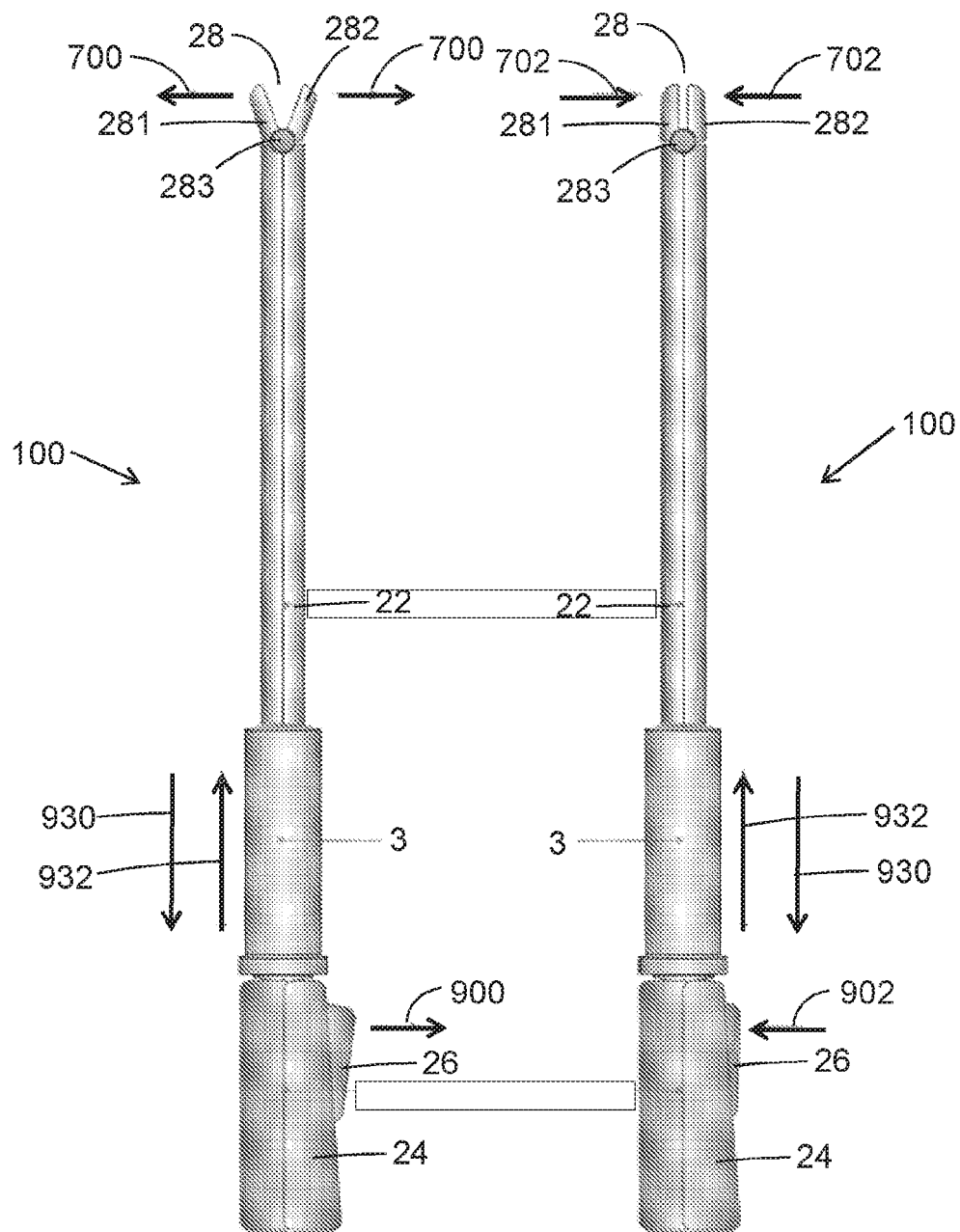
FIGS. 8A and 8B schematically illustrate, according to an exemplary embodiment, an assembled applicator.

FIGS. 8A and 8B schematically illustrate, according to an exemplary embodiment, an assembled applicator 100. According to some embodiments, a stem 22 of a body 2 of the applicator 100 is configured to be inserted into an internal space of an assembled cartridge 3, including a tendon grasping device 1 inserted in the cartridge 3, thus forming an assembled applicator 100. Furthermore, according to one embodiment, the assembled cartridge 3 is configured to slide along the stem 22, either towards the gripper 28, as indicated with arrow 932, or towards the handle 24, as indicated with arrow 930.

According to some embodiments, the gripper 28 may be in an open state or a closed state. FIG. 8A schematically illustrates, according to an exemplary embodiment, an assembled applicator 100 with a gripper 28 in an open state, and FIG. 8B schematically illustrates, according to an exemplary embodiment, an assembled applicator 100 with a gripper 28 in a closed state. According to one embodiment, the first jaw 281 and the second jaw 282 of the gripper 28 may axially move apart from each other, as indicated with arrows 700 in FIG. 8A, thus bringing the gripper 28 to an open state. According to another embodiment, the first jaw 281 and the second jaw 282 of the gripper 28 may axially move towards each other, as indicated with arrows 702 in FIG. 8B, thus bringing the gripper 28 to a close state. According to yet another embodiment, a gripper 28 in a closed state is configured to grip a tendon or an end of a tendon stump. According to a further embodiment, a gripper 28 in an open state is configured to release a tendon or an end of a tendon stump that was previously gripped by the gripper 28. According to yet a further embodiment, an applicator 100 with a gripper 28 in an open state is configured to reach a tendon or an end of a tendon stump before gripping the tendon or the end of a tendon stump.

According to some embodiments, the button 26 attached to the handle 24 is configured to actuate the gripper 28. Thus, as described above, the button 26 is connected to the gripper 28. According to one embodiment, the button 26 may be in either one of two states: pressed as indicated in FIG. 8A, or release as indicated in FIG. 8B. Changing the state of the button 26 from a pressed state to releases state, or vice versa, causes the gripper 28 to change from an open state to a closed state, respectively.

According to a preferred embodiment, the button 26 further comprises an elastic member (not shown), for example by not limited to, a spring, elastic sponge, and the like. According to one embodiment, due to the nature of the elastic member, the default state of the button 26 is the released state, where the button 26 is moved outwards as indicated with arrow 900 in FIG. 8A, Pressing the button 26 inwards as indicated with arrow 902 in FIG. 8B, brings the button 26 to a pressed state. Releasing pressure from the button 26 causes movement of the button 26 outwardly in the direction indicated with arrow 900 (FIG. 8A) due to the elastic nature of the elastic member attached to the button 26.

According to another preferred embodiment, pressing the button 26 in direction 902 causes the first jaw 281 and the second jaw 282 of the gripper 28 to axially move towards each other, as indicated with arrows 700 in FIG. 8B, thus bringing the gripper 28 to a closed state. According to yet another preferred embodiment, releasing the button 26 causes the button 26 to move in direction 900 due to the action of the elastic member, thus causing the first jaw 281 and the second jaw 282 of the gripper 28 to axially move apart from each other, as indicated with arrows 700 in FIG. 1A, thus bringing the gripper 28 to an open state.

According to some embodiments, the internal cylinder 32 of the cartridge 3 is configured to slide inwardly or outwardly inside the external cylinder 38 of the cartridge 3. According to one embodiment, the internal cylinder 32 is configured to slide inwardly or outwardly inside the external cylinder 38 also when the applicator 100 is assembled and a stem 22 of a body 2 of the applicator 100 is inserted into an internal space of the cartridge 3.

According to the embodiment illustrated, for example, in FIGS. 8A-B, the stem 22 is straight, According to another embodiment, the stem 22 is bent.

Figures 9A, 9B:
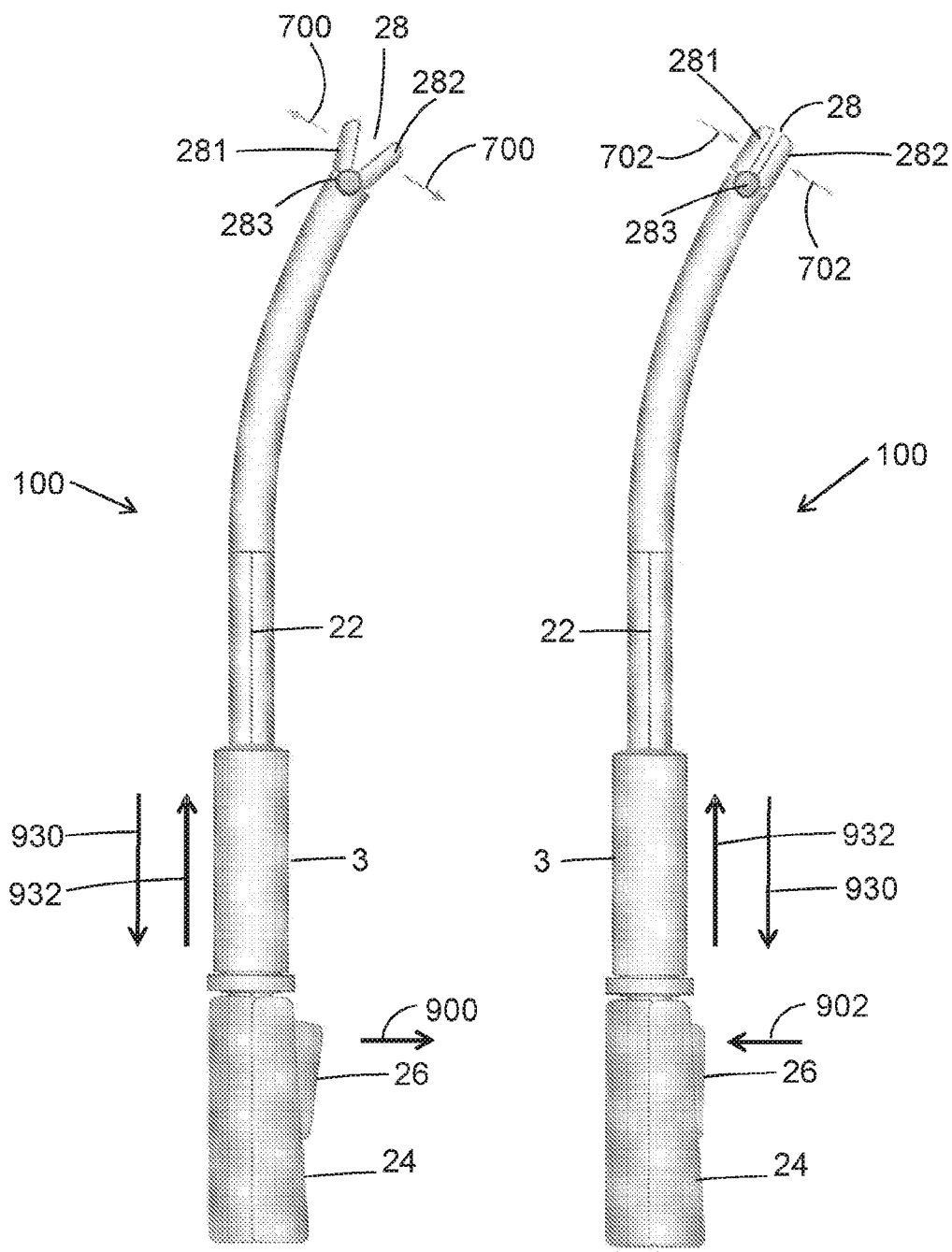
FIGS. 9A-B schematically illustrate, according to an exemplary embodiment, an assembled applicator, comprising a bent stem.

FIGS. 9A-B schematically illustrate, according to an exemplary embodiment, an assembled applicator 100, comprising a bent stem 22. All the features illustrated in FIGS. 9A-B are similar to the features illustrated, for example, in FIGS. 8A-B, except that that stem 22 is bent. According to one embodiment, the stem 22 is permanently bent. According to another embodiment, the stem 22 is bendable, namely, the stem 22 is made of a material that is configured to be bent at any point along the stem 22, and to any angle, as desired. According to yet another embodiment, the stem 22 is configured to easily pass through tissues during treatment of tendon. This may be achieved, for example, according to one embodiment, by making the stem 22 slightly bent, and according to another embodiment, by making the stem 22 flexible.

Figures 10A, 10B, 10C:
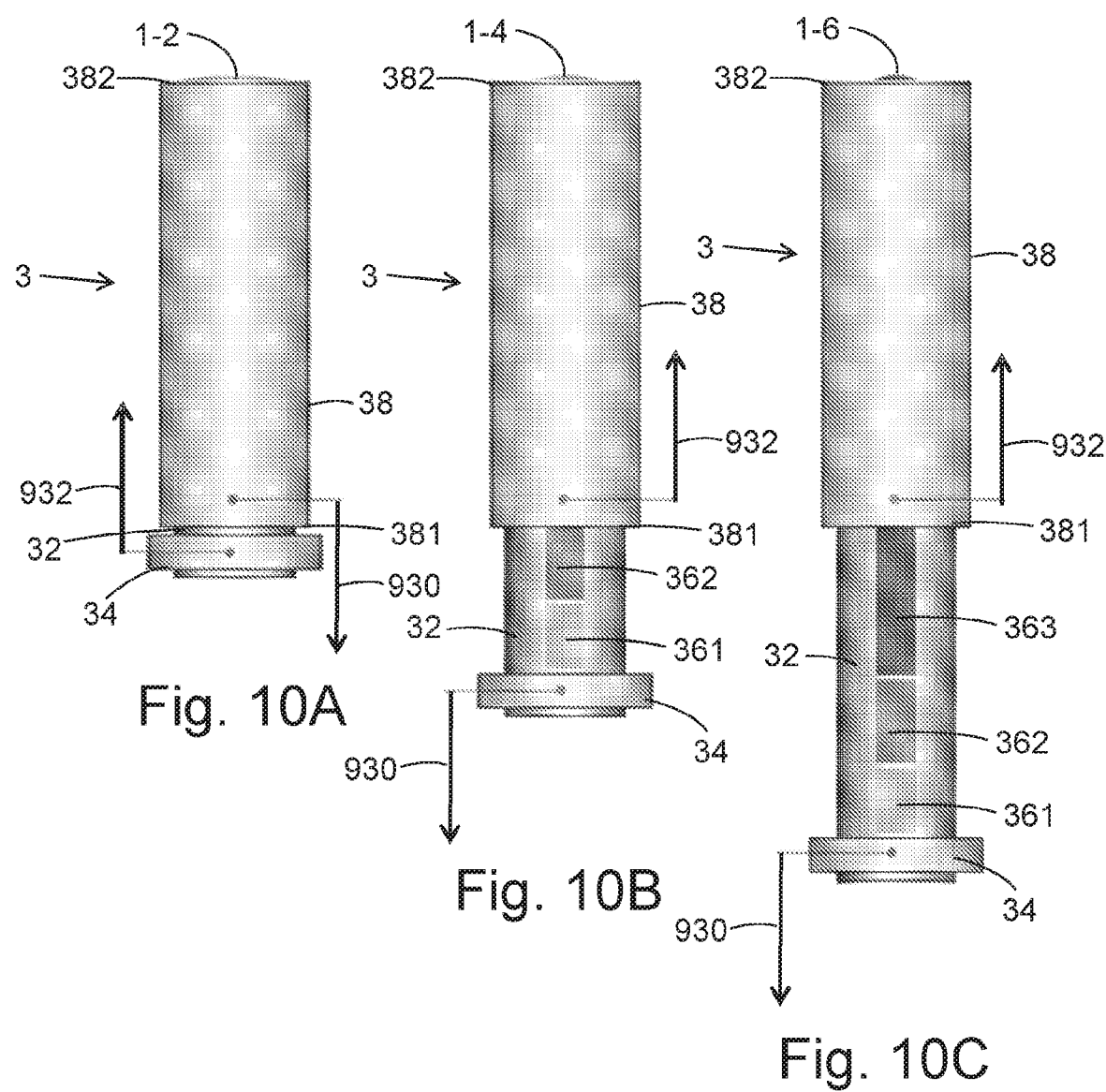
FIGS. 10A-C schematically illustrate, according to exemplary embodiments, an anteroposterior view of a cartridge in three exemplary states of sliding of an internal cylinder sliding inside an external cylinder of a cartridge.

FIGS. 10A-C schematically illustrate, according to exemplary embodiments, an anteroposterior view of a cartridge 3 in three exemplary states of sliding of an internal cylinder 32 sliding inside an external cylinder 38 of a cartridge.

FIG. 10A schematically illustrates, according to an exemplary embodiment, an internal cylinder 32 of a cartridge 3 fully inserted in an external cylinder 38 of the cartridge 3. This may be achieved by either moving the external cylinder 38 in direction 930 until the first opening 381 of the external cylinder 38 engages with the stopper 34 of the internal cylinder 32, or moving the internal cylinder 32 in direction 932 until the stopper 34 of the internal cylinder 32 engages with the first opening 381 of the external cylinder 38, or a combination thereof. According to one embodiment, when the internal cylinder 32 is fully inserted in the external cylinder 38, the index 36 is fully concealed by the external cylinder 38, as illustrated in FIG. 10A. According to another embodiment, the internal cylinder 32 may be inserted in the external cylinder 38 in a manner that allows viewing of the first marking 361 of the index 36, designating "full compression of the tendon grasping device 1" (not shown). Furthermore, an edge of a loose tendon grasping device 1-2 is seen extending from the second opening 382 of the external cylinder 38.

FIG. 10B schematically illustrates, according to an exemplary embodiment, an internal cylinder 32 of a cartridge 3 partially pulled-out from an external cylinder 38 of the cartridge 3. This may be achieved by either moving the external cylinder 38 in direction 932, or moving the internal cylinder 32 in direction 930, or a combination thereof. In all cases the result is that the stopper 34 of the internal cylinder 32 moves away from the first opening 381 of the external cylinder 38. According to one embodiment, when the internal cylinder 32 is partially pulled-out from the external cylinder 38, the index is partially covered, thus allowing viewing of the first marking 361 and the second marking 362 of the index 36, designating "mild extension of the tendon grasping device 1", Furthermore, an edge of a contacting tendon grasping device 1-4 is seen extending from the second opening 382 of the external cylinder 38.

FIG. 10C schematically illustrates, according to an exemplary embodiment, an internal cylinder 32 of a cartridge 3 fully pulled-out from an external cylinder 38 of the cartridge 3. This may be achieved by either moving the external cylinder 38 in direction 932, or moving the internal cylinder 32 in direction 930, or a combination thereof. In all cases the result is that the stopper 34 of the internal cylinder 32 moves away from the first opening 381 of the external cylinder 38. According to one embodiment, when the internal cylinder 32 is fully pulled-out from the external cylinder 38, the index is uncovered, thus allowing viewing of the first marking 361, the second marking 362, and the third marking 363 of the index 36, designating "full extension of the tendon grasping device 1". Furthermore, an edge of a squeezing tendon grasping device 1-6 is seen extending from the second opening 382 of the external cylinder 38.

Figures 11A, 11B, 11C:
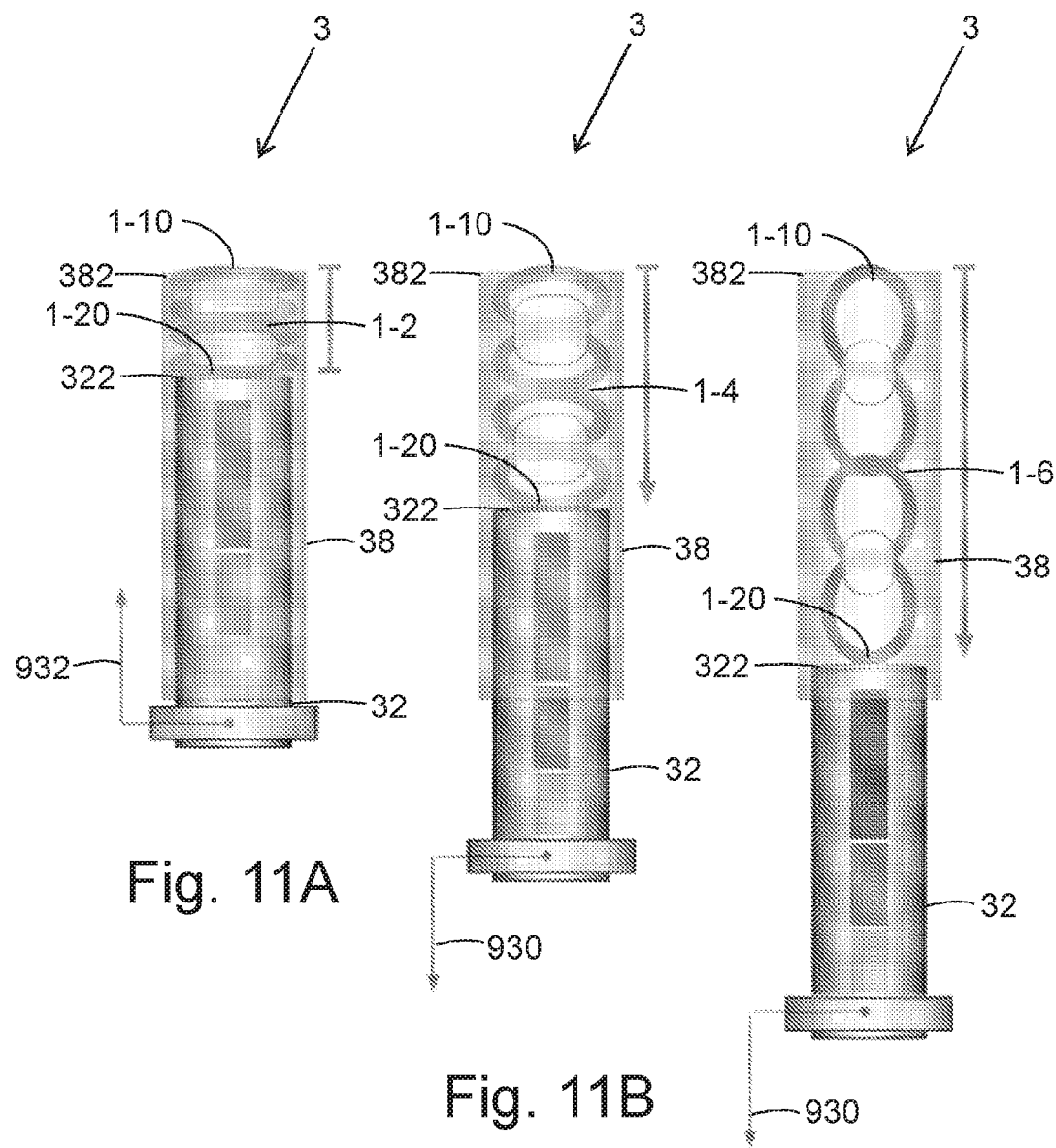
FIGS. 11A and 12A schematically illustrate, according to an exemplary embodiment, an anteroposterior view and a lateral view, respectively, of a cartridge comprising a tendon grasping device, when an internal cylinder of the cartridge is fully inserted in an external cylinder of the cartridge, showing a see-through view through the external cylinder.
FIGS. 11B and 12B schematically illustrate, according to an exemplary embodiment, an anteroposterior view and a lateral view, respectively, of a cartridge comprising a tendon grasping device, when an internal cylinder of the cartridge is partially pulled-out from an external cylinder of the cartridge, showing a see-through view through the external cylinder.
FIGS. 11C and 12C schematically illustrate, according to an exemplary embodiment, an anteroposterior view and a lateral view, respectively, of a cartridge comprising a tendon grasping device, when an internal cylinder of the cartridge is fully pulled-out from an external cylinder of the cartridge, showing a see-through view through the external cylinder.
Figures 12A, 12B, 12C:
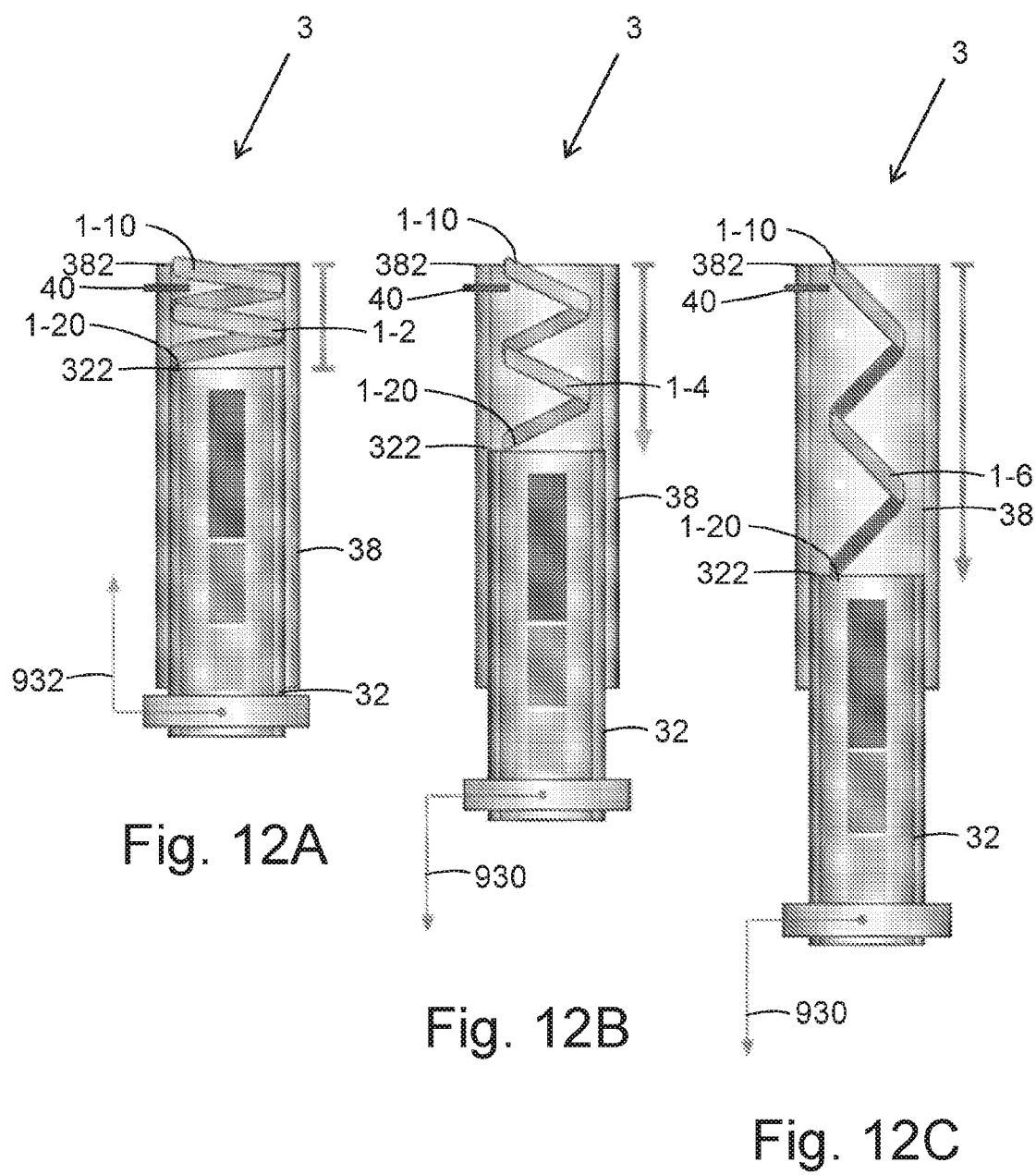

FIGS. 11A and 12A schematically illustrate, according to an exemplary embodiment, an anteroposterior view and a lateral view, respectively, of a cartridge 3 comprising a tendon grasping device 1, when an internal cylinder 32 of the cartridge 3 is fully inserted in an external cylinder 38 of the cartridge 3, showing a see-through view through the external cylinder 38. Embodiments of FIGS. 11A and 12A are similar to embodiments described with regard to FIG. 10A. When the internal cylinder 32 is fully inserted in the external cylinder 38, the tendon grasping device 1-2 is fully compressed and loose.

FIGS. 11B and 12B schematically illustrate, according to an exemplary embodiment, an anteroposterior view and a lateral view, respectively, of a cartridge 3 comprising a tendon grasping device 1, when an internal cylinder 32 of the cartridge 3 is partially pulled-out from an external cylinder 38 of the cartridge 3, showing a see-through view through the external cylinder 38. Embodiments of FIGS. 11B and 12B are similar to embodiments described with regard to FIG. 10B, When the internal cylinder 32 is partially pulled-out from the external cylinder 38, the tendon grasping device 1-4 is mildly extended and in a contacting state, namely contacting a tendon 500.

FIGS. 11C and 12C schematically illustrate, according to an exemplary embodiment, an anteroposterior view and a lateral view, respectively, of a cartridge 3 comprising a tendon grasping device 1, when an internal cylinder 32 of the cartridge 3 is fully pulled-out from an external cylinder 38 of the cartridge 3, showing a see-through view through the external cylinder 38. Embodiments of FIGS. 11C and 12C are similar to embodiments described with regard to FIG. 10C. When the internal cylinder 32 is fully pulled-out from the external cylinder 38, the tendon grasping device 1-6 is fully extended and in a squeezing state, namely squeezing a tendon 500.

According to one embodiment, illustrated in FIGS. 11A-C and 12A-C, once a tendon grasping device 1 is inserted into the cartridge 3, a first end 1-10 of the tendon grasping device 1 is releasably connected to the second opening 382, or substantially adjacent to the second opening 382 of the external cylinder 38; and a second end 1-20 of the tendon grasping device 1 is releasably connected to the second edge 322, or substantially adjacent to the second edge 322 of the internal cylinder 32. According to an additional embodiment, illustrated in FIGS. 12A-C, the external cylinder 38 further comprises a connector 40 attached to an inner surface of the external cylinder 38, substantially adjacent to the second opening 382 of the external cylinder 38. The connector 40 is configured to releasably connect the first end 1-10 of the tendon grasping device 1.

According to one embodiment, when the internal cylinder 32 of the cartridge 3 is fully pulled-out from the external cylinder 38 of the cartridge 3, and the tendon grasping device 1-6 is fully extended and squeezes a tendon 500, further pulling-out of the internal cylinder 32 in direction 930 causes a release of the first end 1-10 of the tendon grasping device 1 from the external cylinder 32, and a release of the second end 1-20 of the tendon grasping device 1 from the internal cylinder 32. According to another embodiment, further pulling-out of the internal cylinder 32 in direction 930 causes a release of the first end 1-10 of the tendon grasping device 1 from the connector 40 attached to an inner surface of the external cylinder 38. According to yet another embodiment, further pulling-out of the internal cylinder 32 in direction 930 causes breakage of the connector 40.

Figures 13A, 13B, 13C:
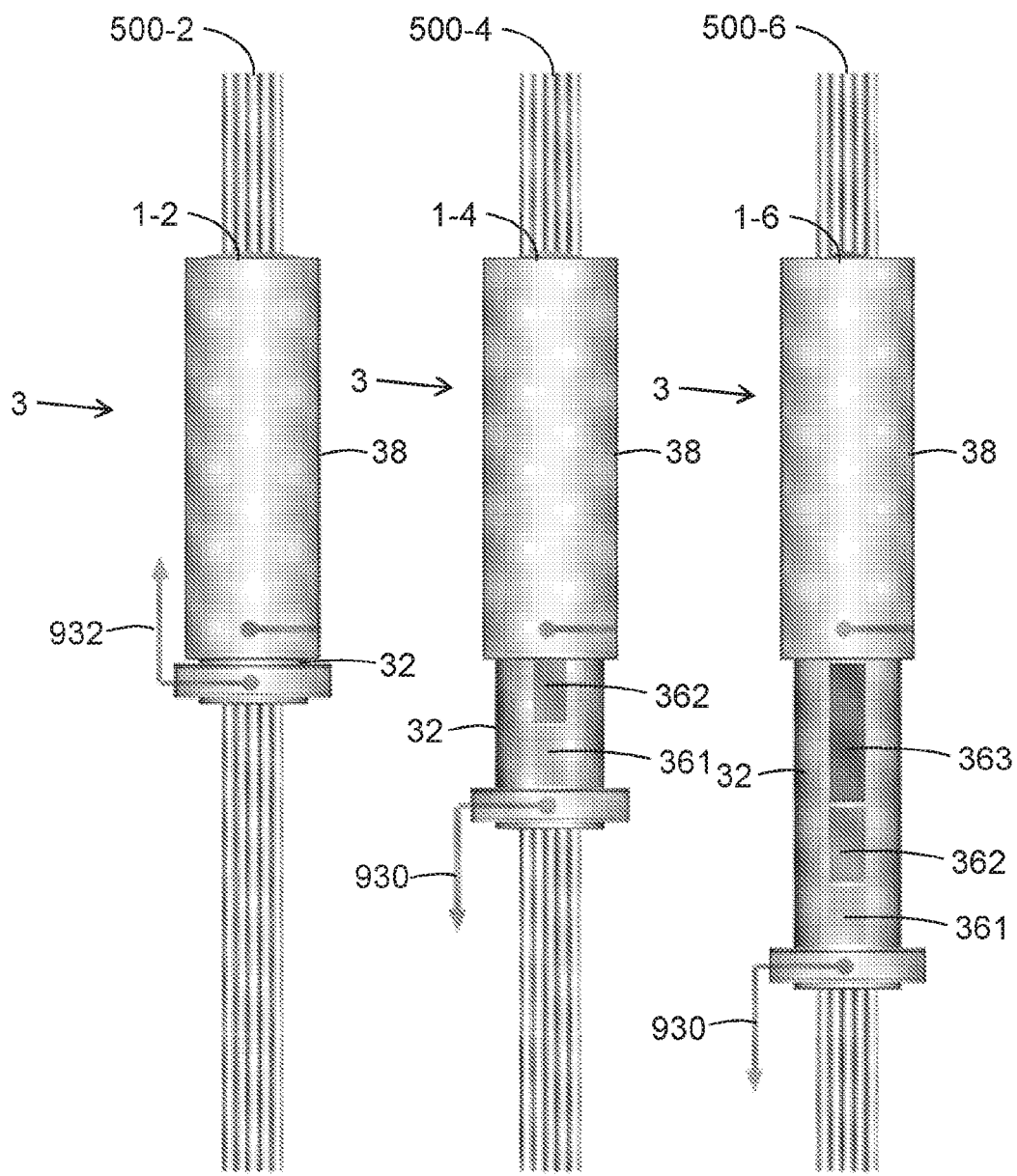
FIG. 13A schematically illustrates, according to an exemplary embodiment, an anteroposterior view of a cartridge comprising a tendon grasping device, when an internal cylinder of the cartridge is fully inserted in an external cylinder of the cartridge, and a tendon is inserted into an inner space of the tendon grasping device.
FIG. 13B schematically illustrates, according to an exemplary embodiment, an anteroposterior view of a cartridge comprising a tendon grasping device, when an internal cylinder of the cartridge is partially pulled-out from an external cylinder of the cartridge, and a tendon is inserted into an inner space of the tendon grasping device.
FIG. 13C schematically illustrates, according to an exemplary embodiment, an anteroposterior view of a cartridge comprising a tendon grasping device, when an internal cylinder of the cartridge is fully pulled-out from an external cylinder of the cartridge, and a tendon is inserted into an inner space of the tendon grasping device.
Figures 14A, 14B, 14C:
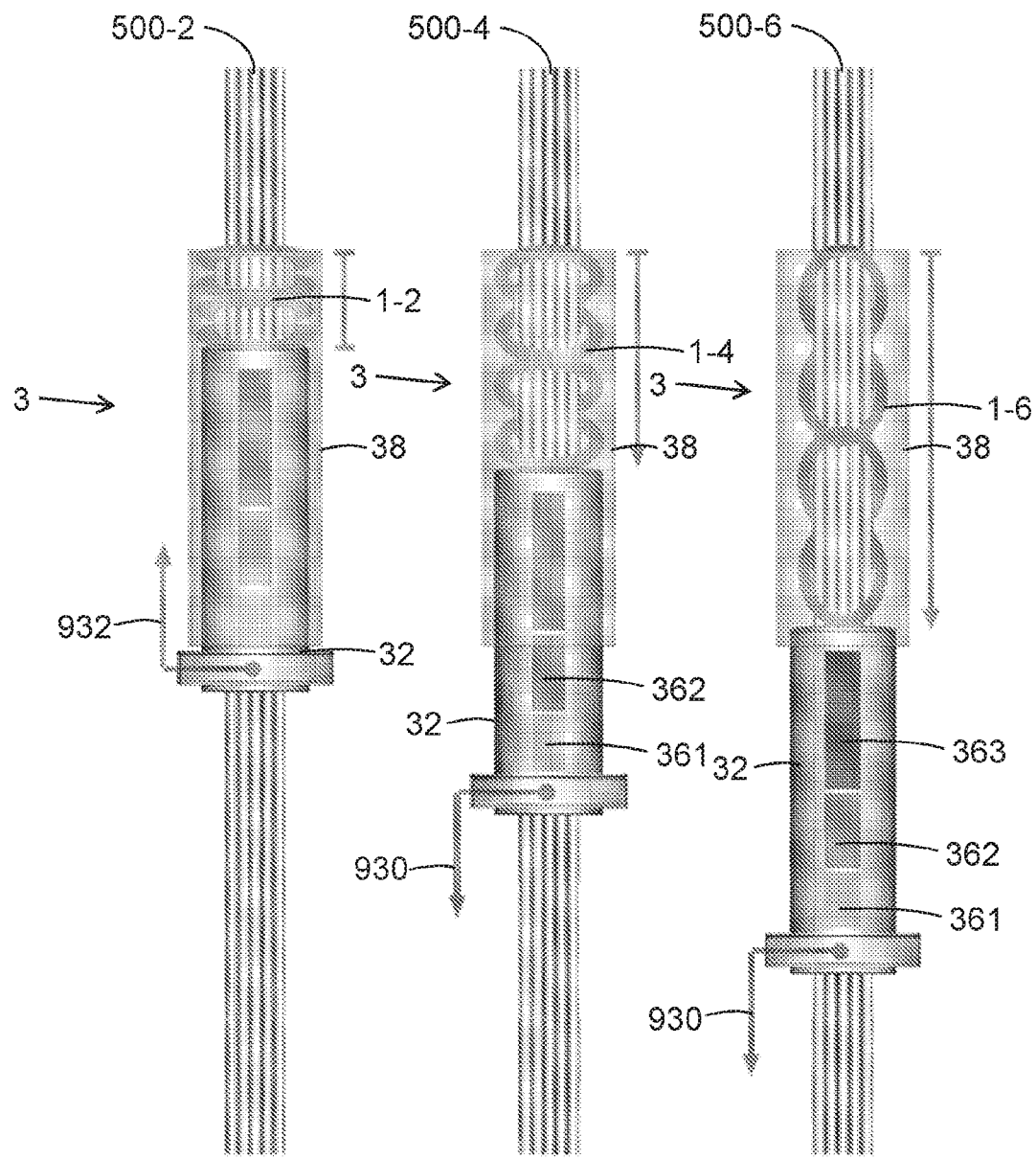
FIG. 14A illustrates the same embodiment as FIG. 13A, showing a see-through view through the external cylinder.
FIG. 14B illustrates the same embodiment as FIG. 13B, showing a see-through view through the external cylinder.
FIG. 14C illustrates the same embodiment as FIG. 13C, showing a see-through view through the external cylinder.

FIG. 13A schematically illustrates, according to an exemplary embodiment, an anteroposterior view of a cartridge 3 comprising a tendon grasping device 1, when an internal cylinder 32 of the cartridge 3 is fully inserted in an external cylinder 38 of the cartridge 3, and a tendon 500 is inserted into an inner space of the tendon grasping device 1. FIG. 14A illustrates the same embodiment as FIG. 13A, showing a see-through view through the external cylinder 38. Embodiments of FIGS. 13A and 14A are similar to embodiments described with regard to FIGS. 10A, 11A and 12A. When the internal cylinder 32 is fully inserted in the external cylinder 38, the tendon grasping device 1-2 is fully compressed and loose, and the tendon 500-2 is loose.

FIG. 13B schematically illustrates, according to an exemplary embodiment, an anteroposterior view of a cartridge 3 comprising a tendon grasping device 1, when an internal cylinder 32 of the cartridge 3 is partially pulled-out from an external cylinder 38 of the cartridge 3, and a tendon 500 is inserted into an inner space of the tendon grasping device 1. FIG. 14B illustrates the same embodiment as FIG. 13B, showing a see-through view through the external cylinder 38. Embodiments of FIGS. 13B and 14B are similar to embodiments described with regard to FIGS. 10B, 11B and 12B. When the internal cylinder 32 is partially pulled-out from the external cylinder 38, the tendon grasping device 1-4 is mildly extended and in a contacting state, and the tendon 500-4 is contacted by the tendon grasping device 1.

FIG. 13C schematically illustrates, according to an exemplary embodiment, an anteroposterior view of a cartridge 3 comprising a tendon grasping device 1, when an internal cylinder 32 of the cartridge 3 is fully pulled-out from an external cylinder 38 of the cartridge 3, and a tendon 500 is inserted into an inner space of the tendon grasping device 1. FIG. 14C illustrates the same embodiment as FIG. 13C, showing a see-through view through the external cylinder 38. Embodiments of FIGS. 13C and 14C are similar to embodiments described with regard to FIGS. 10C, 11C and 12C. When the internal cylinder 32 is fully pulled-out from the external cylinder 38, the tendon grasping device 1-6 is fully extended and in a squeezing state, and the tendon 500-6 is squeezed by the tendon grasping device 1.

FIGS. 15A-F summarize the three major states of grasping a tendon 500 with a tendon grasping device 1. According to some exemplary embodiments, FIGS. 15A and 15B schematically illustrate, according to an exemplary embodiment, an anterior view and a posterior view, respectively, of a loose tendon grasping device 1-2 grasping a loose tendon 500-2. At the loose stage, the loose tendon grasping device 1-2 is fully compressed, and the hollow cylinder-like structure defined by the loose tendon grasping device 1-2 is wider than the loose tendon 500-2. Therefore, when a loose tendon 500-2 is inserted into the hollow space defined by the cylinder-like structure of the loose tendon grasping device 1-2 there is a gap between the loose tendon 500-2 and the loose tendon grasping device 1-2. This allows easy positioning of the loose tendon grasping device 1-2 over a desired site along the loose tendon 500-2.

FIGS. 15C and 15D schematically illustrate, according to an exemplary embodiment, an anterior view and a posterior view, respectively, of a contacting tendon grasping device 1-4 contacting a contacted tendon 500-2. This is achieved by mildly stretching the loose tendon grasping device 1-2 until it comes in contact with the tendon 500. At the contact state, the contacting tendon grasping device 1-4 is mildly extended, and there is no gap between the contacting tendon grasping device 1-4 and the contacted tendon 500-4. Furthermore, the contacted tendon 500-4 is slightly distracted due to a slight pressure exerted on the contacted tendon 500-4 by the contacting tendon grasping device 1-4.

FIGS. 15E and 16F schematically illustrate, according to an exemplary embodiment, an anterior view and a posterior view, respectively, of a squeezing tendon grasping device 1-6 squeezing a squeezed tendon 500-6. This is achieved by further stretching the contacting tendon grasping device 1-4 until it tightly grasps the tendon 500. At the squeeze state, the squeezing tendon grasping device 1-6 is fully extended. Furthermore, the squeezed tendon 500-6 is highly distracted due to a high pressure exerted on the squeezed tendon 500-6 by the squeezing tendon grasping device 1-6.

Figures 16A, 16B, 16C:
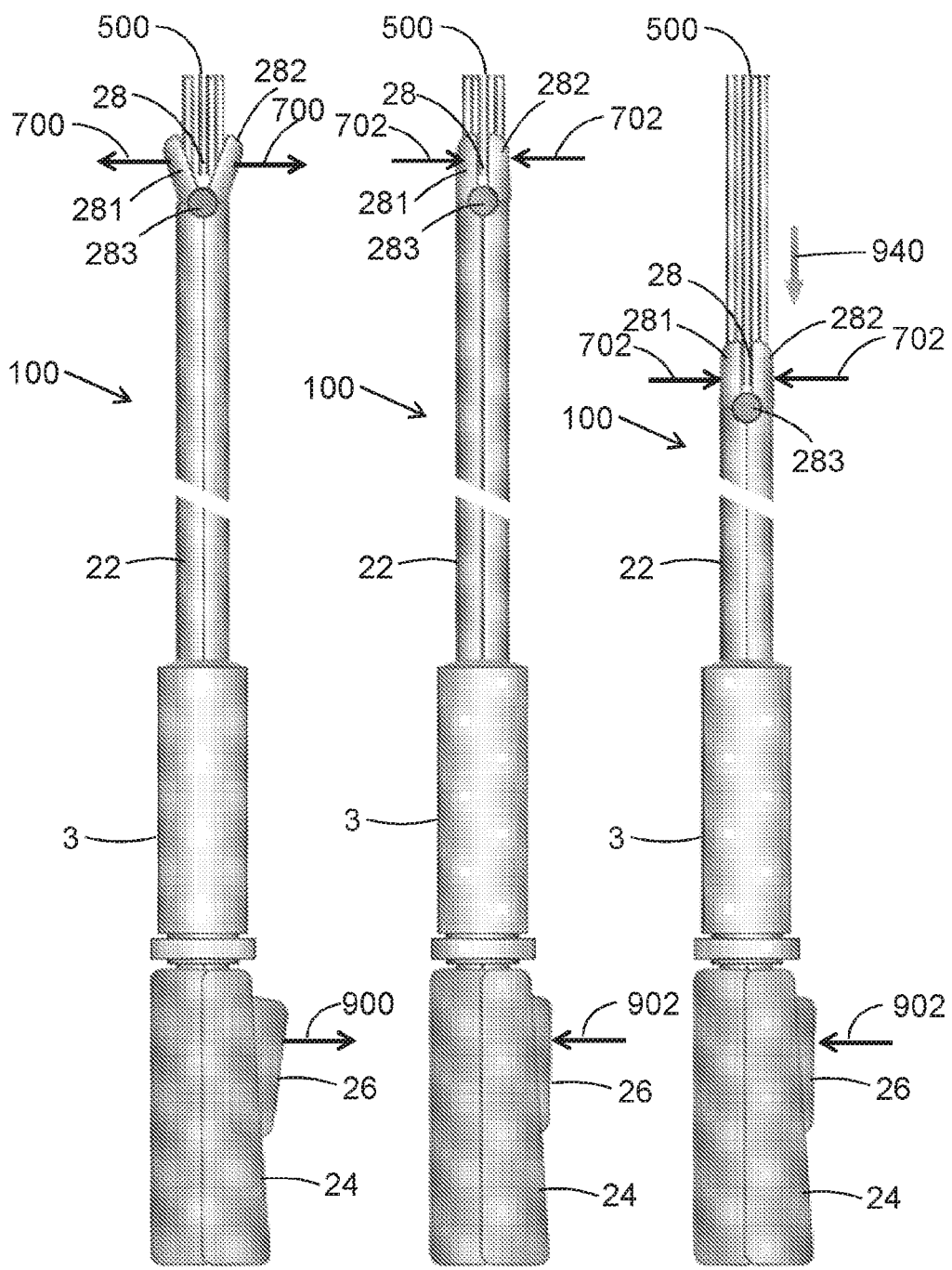
FIGS. 16A-C schematically illustrate, according to an exemplary embodiment, stages of gripping and pulling a tendon with an applicator.

FIGS. 16A-C schematically illustrate, according to an exemplary embodiment, stages of gripping and pulling a tendon 500 with an applicator 100. The applicator 100 and its function are described in detail in FIGS. 8A-B. In FIG. 16A, the gripper 28 is in an open state, adjacent to an end of a tendon 500 or a tendon 500 stump. In FIG. 16B, the gripper 28 is in a closed state due to pressing the button 26 in direction 902. Thus, the end of the tendon 500 or of the tendon 500 stump is gripped by the closed gripper 28. In FIG. 16C, the gripped tendon 500 or tendon 500 stump may be pulled, for example to make access for the tendon grasping device 1 or to bring the tendon 500 stump end close to another tendon 500 stump end. The gripped tendon 500 or tendon 500 stump may be pulled in the direction designated with arrow 940, for example by shortening the stem 22 in embodiments where the stem is telescopic.

Figures 17A, 17B, 17C, 17D:
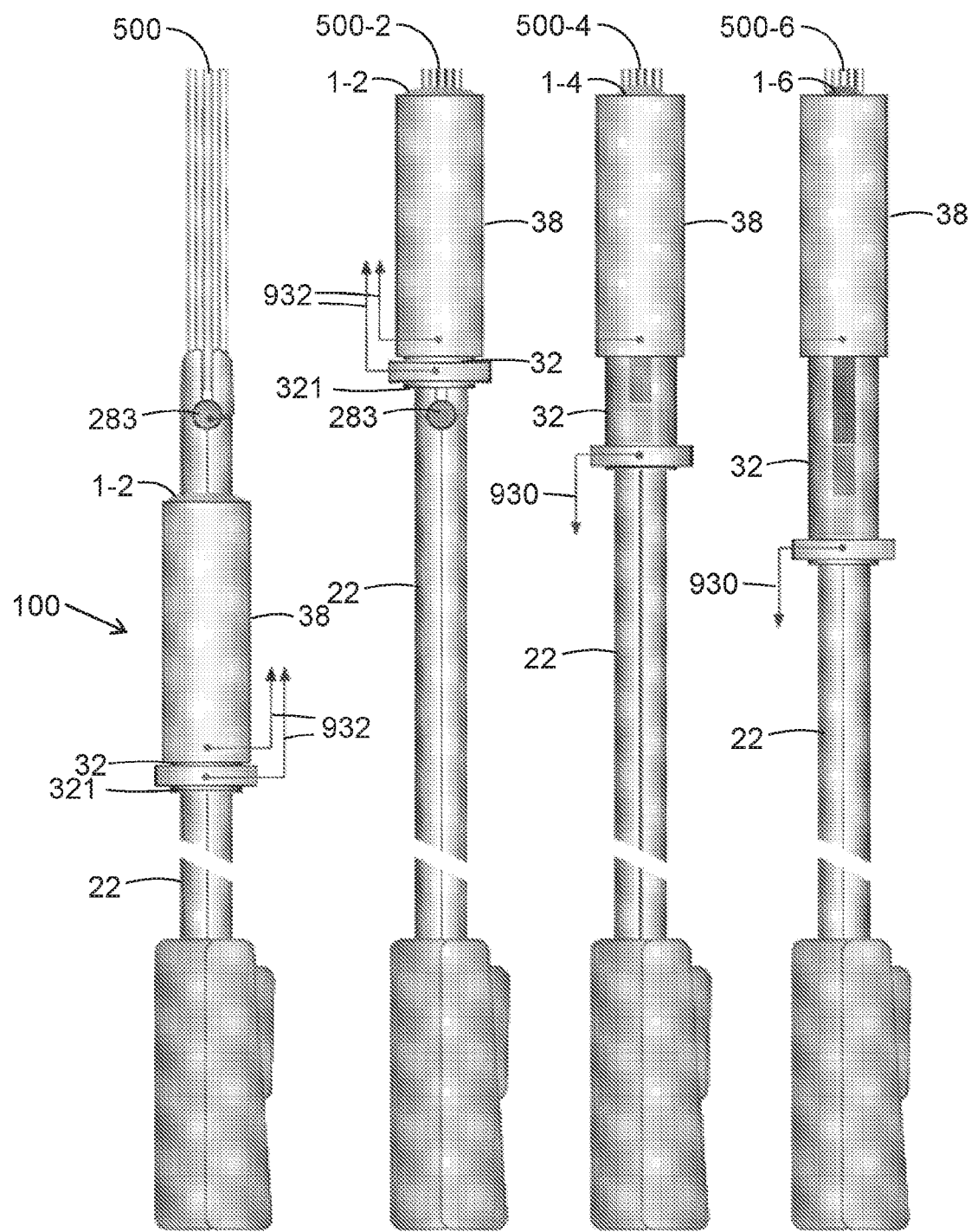
FIGS. 17A-D schematically illustrate, according to an exemplary embodiment, stages of grasping a tendon or tendon stump, gripped by an applicator, with a tendon grasping device.

FIGS. 17A-D schematically illustrate, according to an exemplary embodiment, stages of grasping a tendon 500 or tendon 500 stump, gripped by an applicator 100, with a tendon grasping device 1. These stages were described in detail, for example in FIGS. 13A-C and 14A-C. After the tendon 500 or tendon 500 stump end is gripped by the applicator 100, as illustrated in FIGS. 16A-C, the cartridge 3 containing a loose tendon grasping device 1-2 in a fully compressed state is slid along the stem 22 towards the tendon 500 or tendon 500 stump end, in direction 932, as illustrated in FIG. 17A. According to a preferred embodiment, illustrated in FIG. 17B, the cartridge 3 is slid until the first edge 321 of the internal cylinder 32 of the cartridge 3 is positioned distally, in direction 932, relative to the axis 283 of the gripper 28. As a result, the tendon 500 is inserted into the internal space defined by the tendon grasping device 1. Grasping of the gripped tendon 500 is achieved by pulling the internal cylinder 32 in direction 930. FIG. 17C schematically illustrates a state where the internal cylinder 32 is partially pulled-out from the external cylinder 38, the tendon grasping device 1-4 is mildly extended and in a contacting state, and the tendon 500-4 is contacted by the tendon grasping device 1. FIG. 17D schematically illustrates a state where the internal cylinder 32 is fully pulled-out from the external cylinder 38, the tendon grasping device 1-6 is fully extended and in a squeezing state, and the tendon 500-6 is squeezed by the tendon grasping device 1.

Figures 18A, 18B, 18C, 18D:
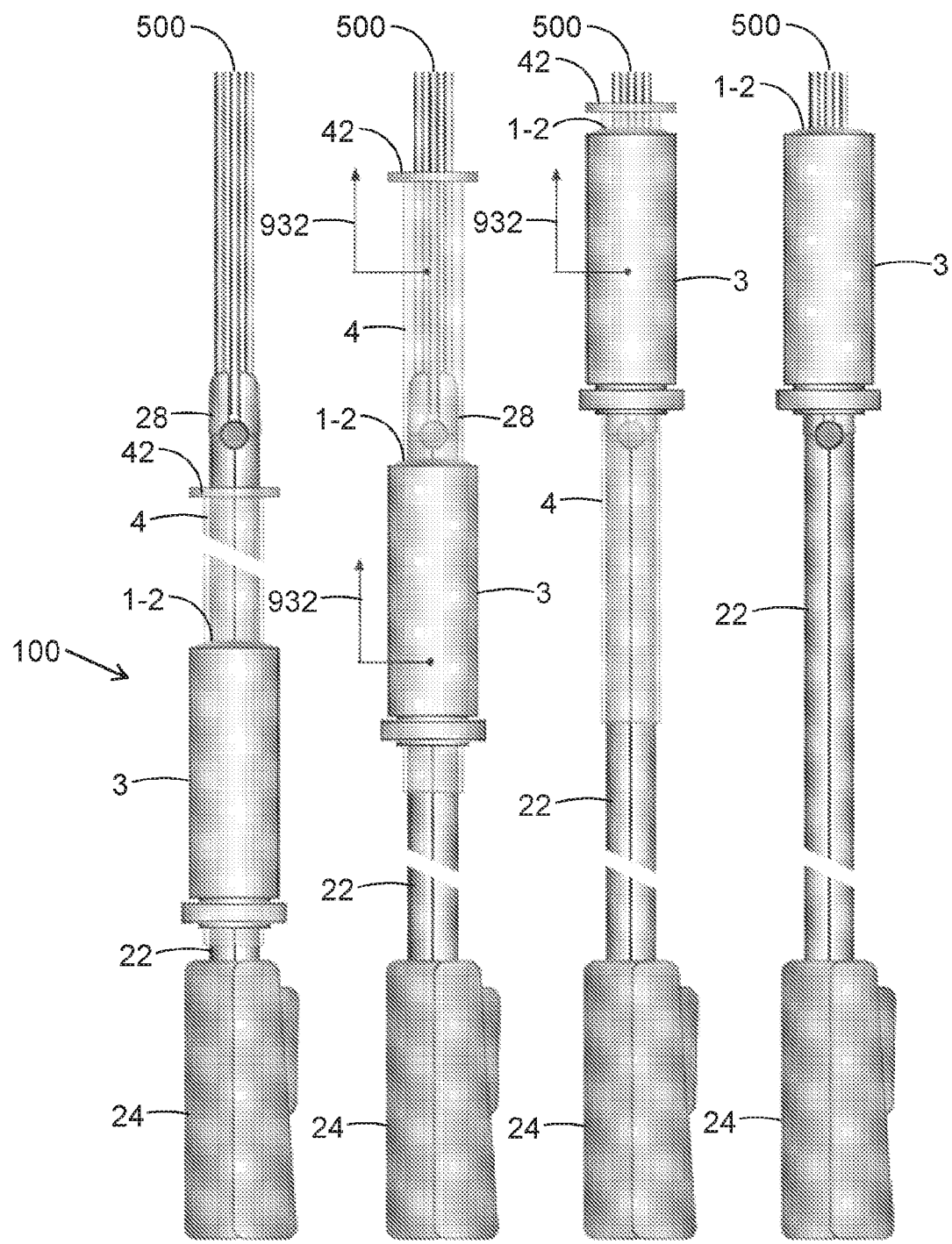
FIGS. 18A-D schematically illustrate, according to an exemplary embodiment, an applicator further comprising a tendon cover, and stages of protecting a tendon with the tendon cover during the positioning of a cartridge containing a tendon grasping device over the tendon.

FIGS. 18A-D schematically illustrate, according to an exemplary embodiment, an applicator 100 further comprising a tendon cover 4, and stages of protecting a tendon 500 with the tendon cover 4 during the positioning of a cartridge 3 containing a tendon grasping device 1 over the tendon 500. According to one embodiment, the tendon cover 4 is cylindrically-shaped. According to another embodiment, the inner diameter of the tendon cover 4 is substantially larger than the diameter of the stem 22, the diameter of the gripper 28 in a closed state, and the diameter of the tendon 500 gripped by the gripper 28, thus enabling sliding of the tendon cover 4 along the stem 22 and over the gripper 28 in a closed state, as well as covering the tendon 500. According to another embodiment, the outer diameter of the tendon cover 4 is substantially smaller than the inner diameter of a fully compressed and loose tendon grasping device 1-2 accommodated in a cartridge, thus allowing sliding of the tendon cover 4 while accommodated in the inner space of a fully compressed and loose tendon grasping device 1-2, while contained in a cartridge 3. According to a further embodiment, the tendon cover 4 is configured to protect a tendon 500 after it was gripped by the gripper 28 and during the positioning of a cartridge 3 containing a tendon grasping device 1 over the tendon 500. According to a preferred embodiment, the tendon cover 4 is made of a flexible material. According to an additional embodiment, the tendon cover 4 further comprises a ring 42 attached to an end of the tendon cover 4 cylindrical structure that is proximal to the gripper 28 of an applicator 100, when the tendon cover 4 is assembled with the applicator 100. According to one embodiment, the inner diameter of the ring 42 is substantially similar to the inner diameter of the tendon cover 4, and the outer diameter of the ring 42 is substantially larger than the outer diameter of the tendon cover 4. According to one embodiment, the ring 42 is configured to serve as a handle while sliding the tendon cover 4 along the stem 22 and over the gripped tendon 500. According to another embodiment, the ring 42 is configured to serve as a stopper, According to this embodiment, when the tendon cover 4 covers a gripped tendon 500, the ring 42 serves as a stopper that does not allow further sliding of the cartridge 3, as illustrated in FIG. 18C. According to an additional embodiment, the diameter of the tendon cover 4 is larger when the tendon cover 4 is compressed. Namely, the tendon cover 4 squeezes the site of the sutured tendon 500 when distracted. According to yet an additional embodiment, the tendon cover 4 resembles a Chinese finger trap, According to still an additional embodiment, the tendon cover 4 is positioned around a ruptured and sutured tendon 500 in a manner resembling a finger glove. According to a further embodiment, the tendon cover 4 is configured to circumferentially compress a site of rupture of a tendon 500, thus minimizing tissue oedema (swelling), and facilitating sliding movements of the restored tendon 500.

In FIG. 18A, an applicator 100 gripping a tendon 500, and a tendon cover 4 accommodated in an inner space of a fully compressed loose tendon grasping device 1-2 that is contained in a cartridge positioned over a stem 22 of the applicator 100. In FIG. 18B, the tendon cover 4 is slid along the stem 22, and over the closed gripper 28 and the gripped tendon, in direction 932. In parallel, the cartridge 3 is slid over the tendon cover 4 in direction 932. In FIG. 18C, the tendon cover 4 is positioned in a desired position over the gripped tendon 500, and the cartridge 3 is slid in direction 932 until it is stopped by the ring 42. In FIG. 18D, the tendon cover 4 is removed from the cartridge in order to allow grasping of the gripped tendon 500 with a tendon grasping device 1 that is accommodated in the cartridge 3. According to one embodiment, the tendon cover 4 is removed from the cartridge 3 by further sliding it along the tendon 500, in direction 932. According to another embodiment, the tendon cover is removed from the cartridge 3 by sliding it along the stem 22 towards the handle 24 of the applicator 100 (not shown).

After a tendon 500 is grasped by a tendon grasping device 1, as described for example in FIG. 17O, namely the internal cylinder 32 is fully pulled-out from the external cylinder 38, the tendon grasping device 1-6 is fully extended and in a squeezing state, and the tendon 500-6 is squeezed by the tendon grasping device 1—the cartridge 3 is removed from the squeezed tendon 500-6, and the squeezed tendon 500-6 is released from the gripping by the gripper 28 of the applicator 100.

Figures 19A, 19B, 19C, 19D, 19E:
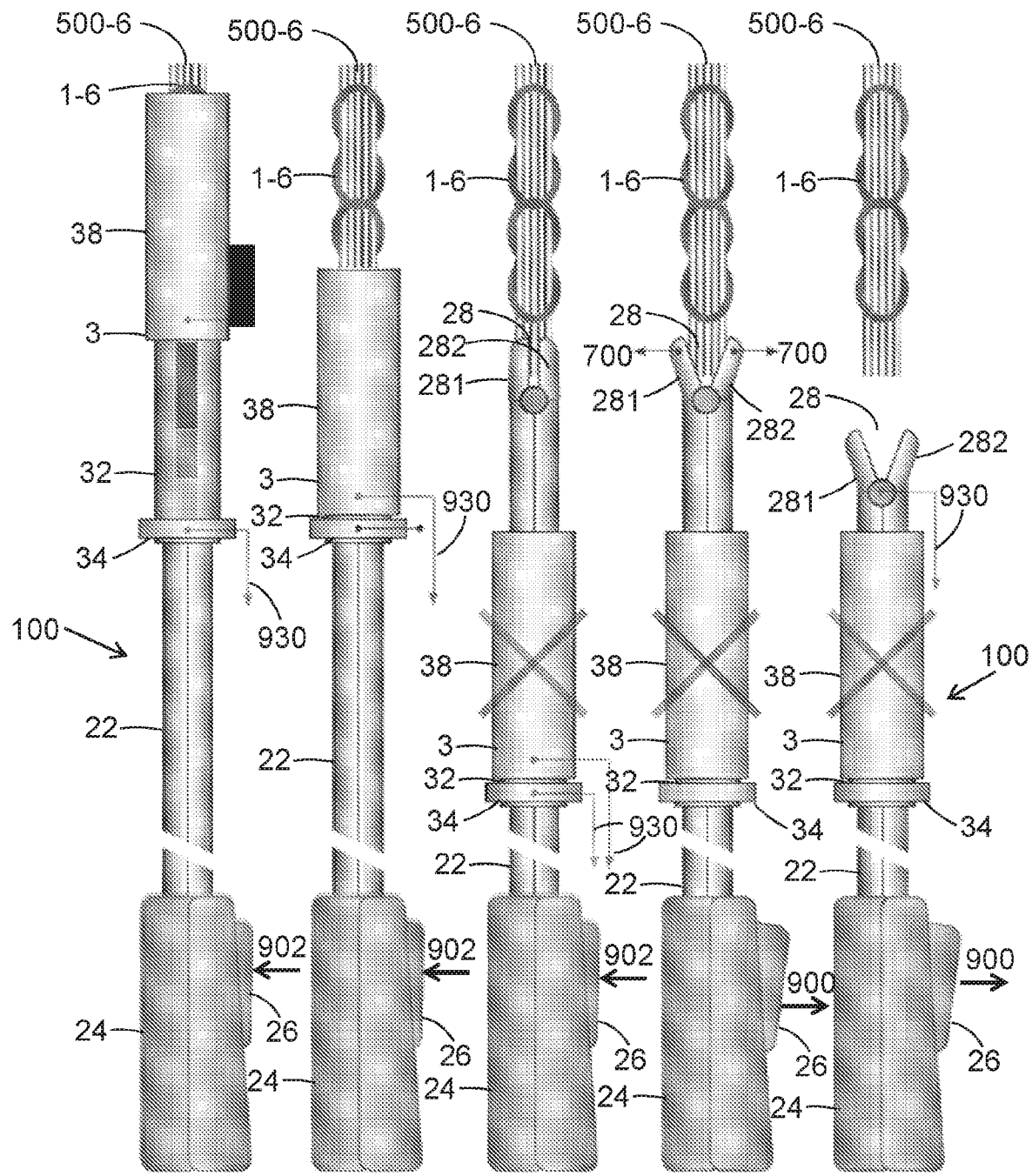
FIGS. 19A-E schematically illustrate, according to an exemplary embodiment, stages of removal of a cartridge from a tendon squeezed by a tendon grasping device, and release of the squeezed tendon from gripping by a gripper of an applicator.

FIGS. 19A-E schematically illustrate, according to an exemplary embodiment, stages of removal of a cartridge 3 from a tendon 500-6 squeezed by a tendon grasping device 1-6, and release of the squeezed tendon 500-6 from gripping by a gripper 28 of an applicator 100. FIG. 19A is similar to FIG. 17D. At this stage the internal cylinder 32 is fully pulled-out from the external cylinder 38, the tendon grasping device 1-6 is fully extended and in a squeezing state, the tendon 500-6 is squeezed by the tendon grasping device 1, and the external cylinder 38 of the cartridge covers the tendon grasping device 1-6 that squeezes the tendon 500-6. In FIG. 19B, the external cylinder 38 is moved along the stem 22 in direction 930, towards the handle 24, until it is stopped by the stopper 34 of the internal cylinder 32. In FIG. 19C, the entire cartridge 3, including the internal cylinder 32 and the external cylinder 38, is moved in along the stem 22 in direction 930, towards the handle 24, until the gripper 28 is exposed. It should be noted that at this stage, the gripper 28 still grips the squeezed tendon 500-6, for example by pressing the button 26 inwards, in direction 902. In FIG. 19D, the squeezed tendon 500-6 is released by bringing the gripper 28 to an open state, namely letting the first jaw 281 and the second jaw 282 of the gripper 28 to axially move apart from each other, as indicated with arrows 700. This may be achieved, for example, by releasing a pressure exerted on the button 26, thus causing the button 26 to move outwards in direction 900. In FIG. 19E, the applicator 1 is removed from the area of the squeezed tendon 500-6.

The present invention further provides a method for grasping a tendon stump with a tendon grasping device 1, comprising:

inserting a tendon stump through a first edge of a fully compressed tendon grasping device 1 into an inner space of the tendon grasping device 1—At this state the dimeter of the cylinder-like structure of the tendon grasping device 1 is maximal, and after inserting the tendon stump into the inner space of the tendon grasping device 1, the tendon grasping device 1 surrounds the tendon stump.

extending the length of the tendon grasping device, while decreasing the diameter of the tendon grasping device, until the tendon grasping device 1 tightly grasps the tendon stump.

With the tendon grasping device 1 tightly grasping the tendon, any pull of the free end of the tendon grasping device 1 i.e. the end of the tendon grasping device 1 that is not attached to the tendon, is transmitted to the tendon and the elements attached thereto.

The present invention further provides a method for reconnecting two stumps of a cut tendon, comprising: inserting a first tendon stump through a first edge of a fully compressed first tendon grasping device 1 into an inner space of the first tendon grasping device 1; extending the length of the first tendon grasping device 1, while decreasing the diameter of the first tendon grasping device 1, until the first tendon grasping device 1 tightly grasps the first tendon stump; inserting a second tendon stump through a first edge of a fully compressed second tendon grasping device 1 into an inner space of the second tendon grasping device 1; extending the length of the second tendon grasping device 1, while decreasing the diameter of the second tendon grasping device 1, until the second tendon grasping device 1 tightly grasps the second tendon stump; and connecting the second edge of the first tendon grasping device 1 grasping the first tendon stump with the second edge of the second tendon grasping device grasping the second tendon stump.

According to one embodiment, extending the length of the tendon grasping device 1 is achieved by pulling the second end of the tendon grasping device 1.

According to another embodiment, the second edge of the first tendon grasping device 1 is connected to the second edge of the second tendon grasping device 1 by connecting a loop substantially adjacent to the second end of the first tendon grasping device 1 with a loop substantially adjacent to the second end of the second tendon grasping device 1, using a connector.

The methods for treating tendon ruptures provided by the present invention have several advantages over prior art procedures: a very short period of time, less than one minute, is necessary for grasping a tendon stump, thus considerably shortening the surgical procedure.

No need for tendon suturing, thus shortening the surgical procedure and recovery period.

A very simple procedure to perform, thus negating the need for a highly skilled surgeon.

Providing a single type of device and procedure suitable for the treatment of all types of tendon rupture.

Providing tendon stabilization forces that allow immediate post-operative full weight bearing and full range movements, compared to prior art procedures which allow only gradual mobilization and weight bearing immediately after the surgical procedure.

No need for post-operative immobilization, compared to need for immobilization lasting 4-8 weeks after the prior art procedures.

Movement, both passive and active, of a limb in which a tendon was treated according to the present invention, as soon as pain subsides.

Figure 20:
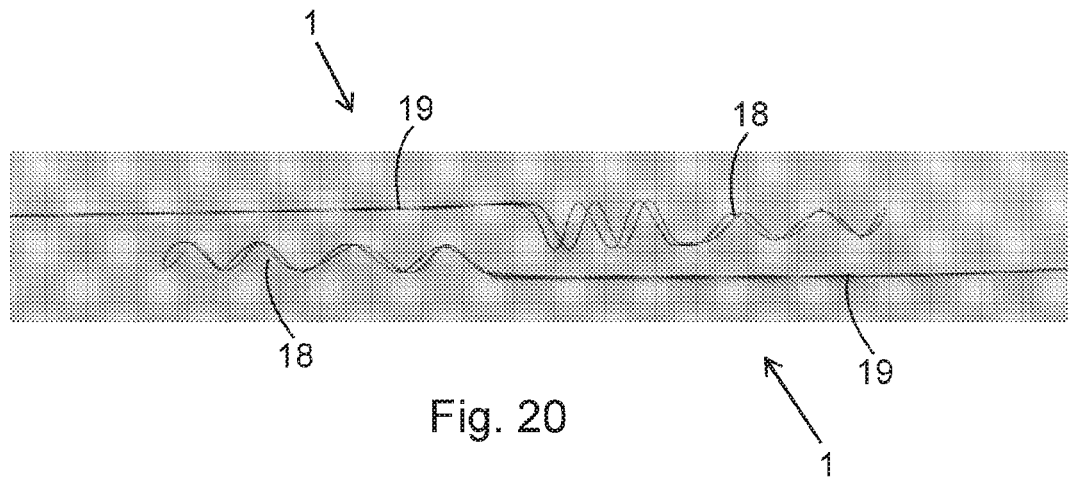
FIGS. 20 and 21 show, according to an exemplary embodiment, an upper perspective view of additional embodiments of the tendon grasping device.
Figure 21:
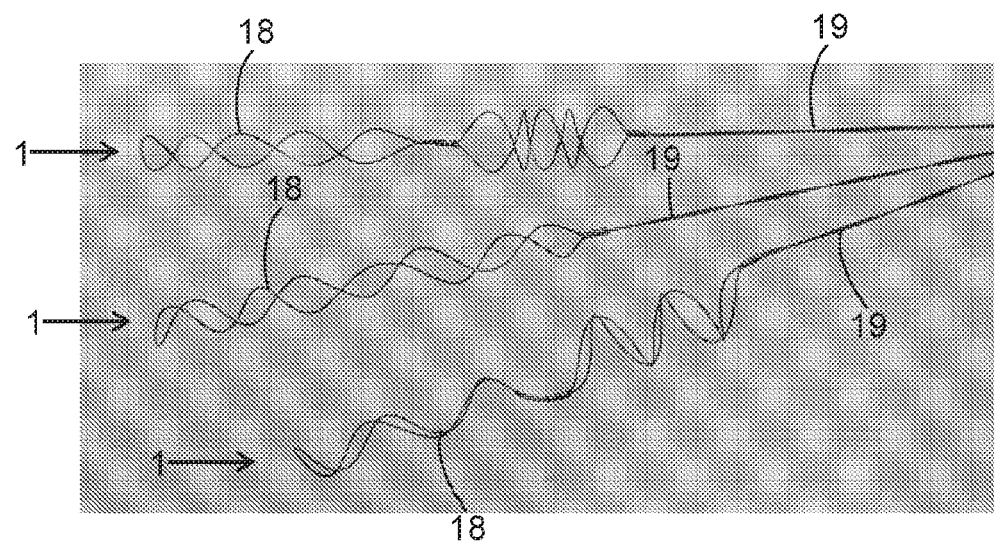

FIGS. 20 and 21 show, according to an exemplary embodiment, an upper perspective view of additional embodiments of the tendon grasping device 1. The structure of the tendon grasping device 1 is according to the embodiments previously described. Additional embodiments of the tendon grasping device 1 are as follows:

According to some embodiments, the tendon grasping device 1 comprises a first part 18 and a second part 19. According to one embodiment, the first part 18 is elastic, namely having shape memory, and the second part 19 is a loose thread. According to another embodiment, both the first part 18 and the second part 19 are elastic. According to yet another embodiment, the first part 18 is loose and the second part 19 is elastic. According to still another embodiment, both the first part 18 and the second part 19 of the tendon grasping device 1 are loose.

According to these embodiments, the elastic part of the tendon grasping device 1—the first part 18 and/or the second part 19, is configured to grasp a tendon 500 naturally, namely without having a user or device tightening the elastic part of the tendon grasping device 1 around a tendon 500. When a tendon 500 stump is inserted into a hollow cylinder-like structure defined by the elastic part of the tendon grasping device 1, or when the elastic part of the tendon grasping device 1 is pulled over a tendon 500 stump, the elastic part is naturally tightened over the tendon 500. On the other hand, when a tendon 500 stump is inserted into a hollow cylinder-like structure defined by a loose part of the tendon grasping device 1, or when the loose part of the tendon grasping device 1 is pulled over a tendon 500 stump, the loose part should be tightened over the tendon 500 by a user and/or a device.

FIGS. 22-32 schematically illustrate, according to an exemplary embodiment, a side perspective view of some additional embodiments of an applicator 100 configured to apply the tendon grasping device 1, having a first part 18 and a second part 19, on a tendon 500 stump.

According to some embodiments, the applicator 100 comprises an inner stem 22 inserted into a hollow sleeve 23, the inner stem 22 is movable inside the hollow sleeve 23. A gripper 28, configured to grip a tendon 500 or an end of a tendon 500 stump, is attached to a first end of the inner stem 22. The gripper 28 may be remotely actuated as described previously. The applicator further comprises at least one handle, for example four handles 24, 25, 27, 29, configured to control the applicator 100. For example, a handle 24 may be attached to an end of the inner stem 22, another handle 27 may be attached to an end of the hollow sleeve 23, a handle 25 may be configured to actuate the gripper 28, and a handle 29 to push the tendon grasping device 1 that is applied over the hollow sleeve 23, out of the hollow sleeve 23. The handle 29 may be connected to a further sleeve, not shown in the Figures, or any other element appropriate to push the tendon grasping device 1, to release it from the sleeve 23.

Figure 22:
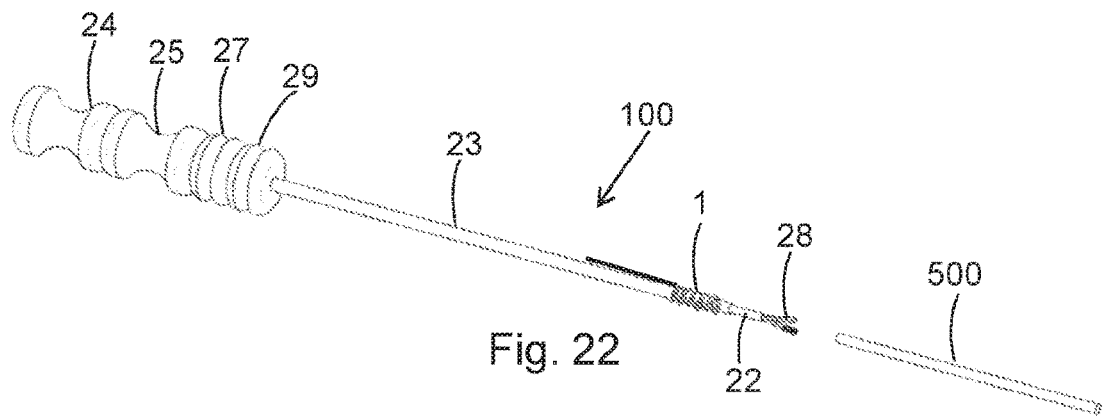
FIGS. 22-32 schematically illustrate, according to an exemplary embodiment, a side perspective view of some additional embodiments of an applicator configured to apply the tendon grasping device, having a first part and a second part, on a tendon stump.
Figure 23:
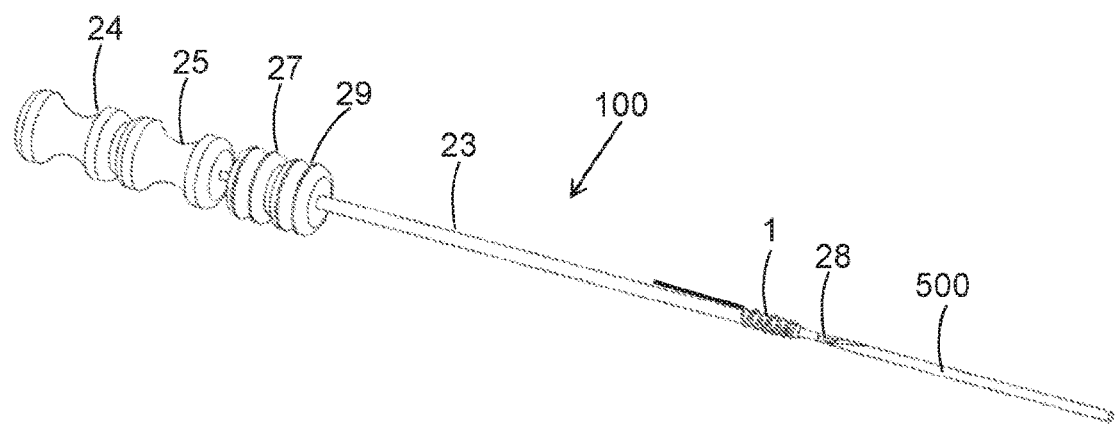
Figure 24:
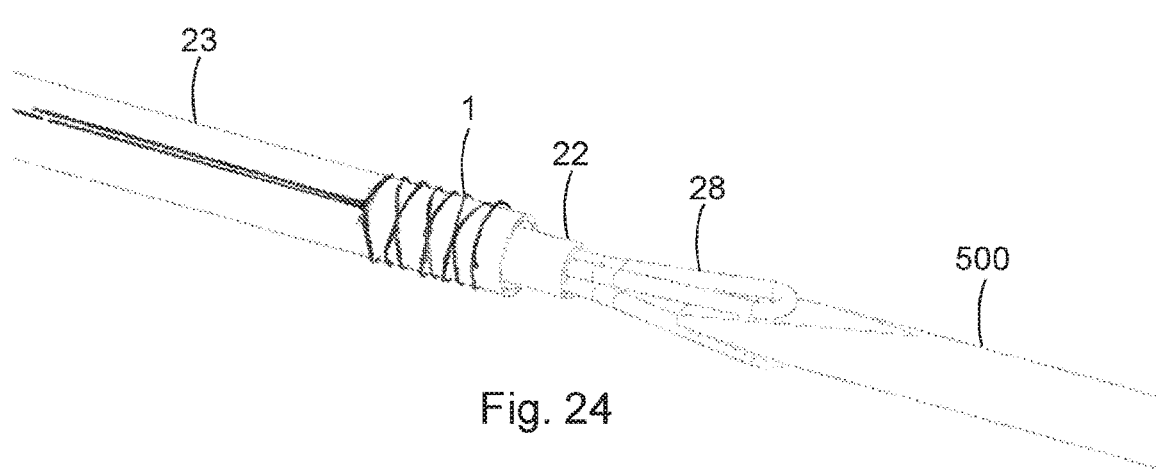
Figure 25:
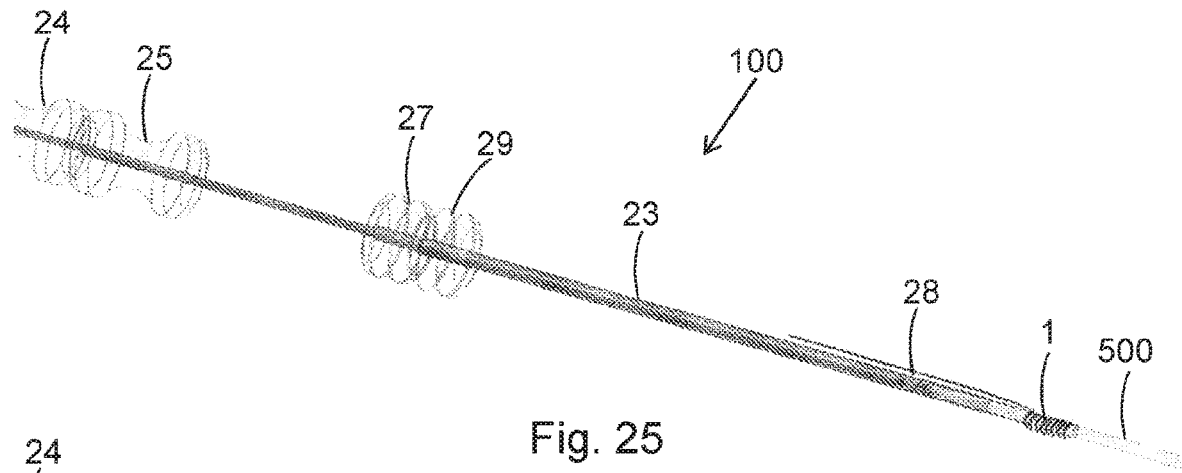
Figure 26:
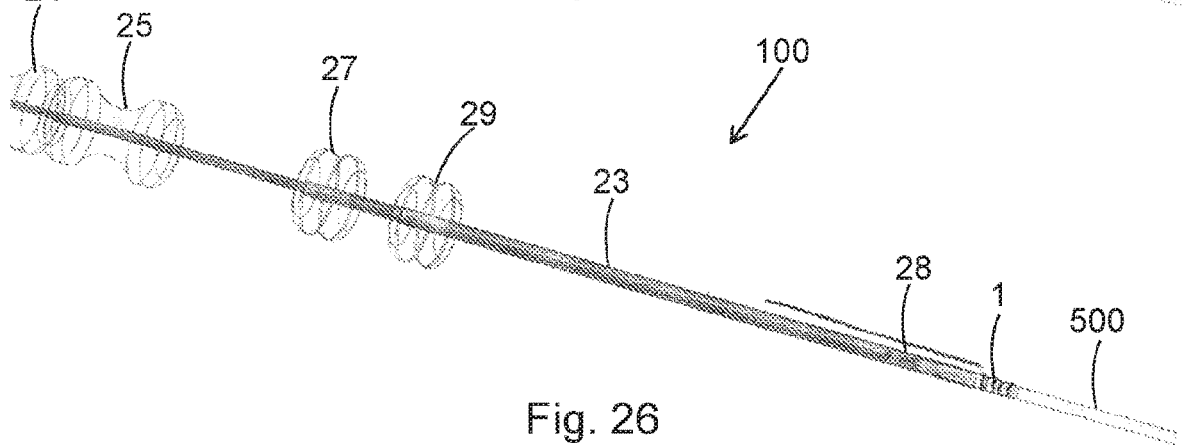
Figure 27:
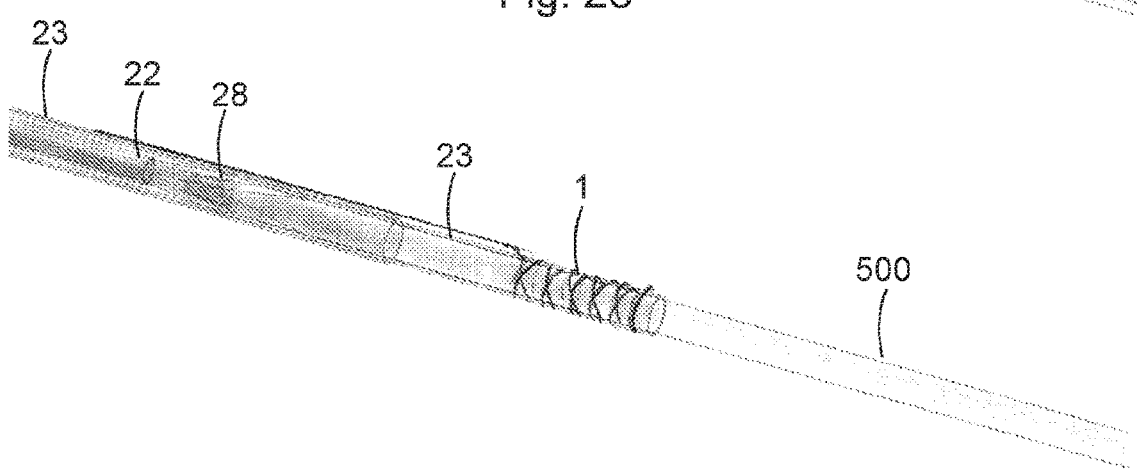
Figure 28:
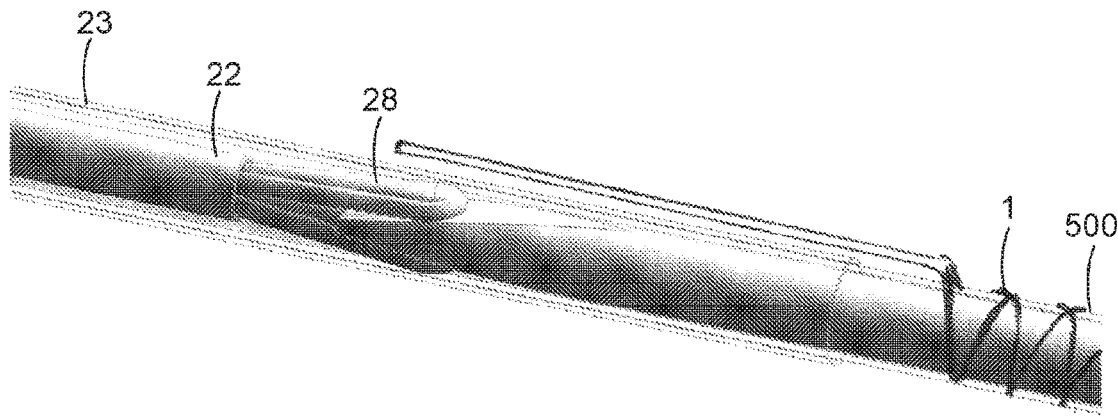
Figure 29:
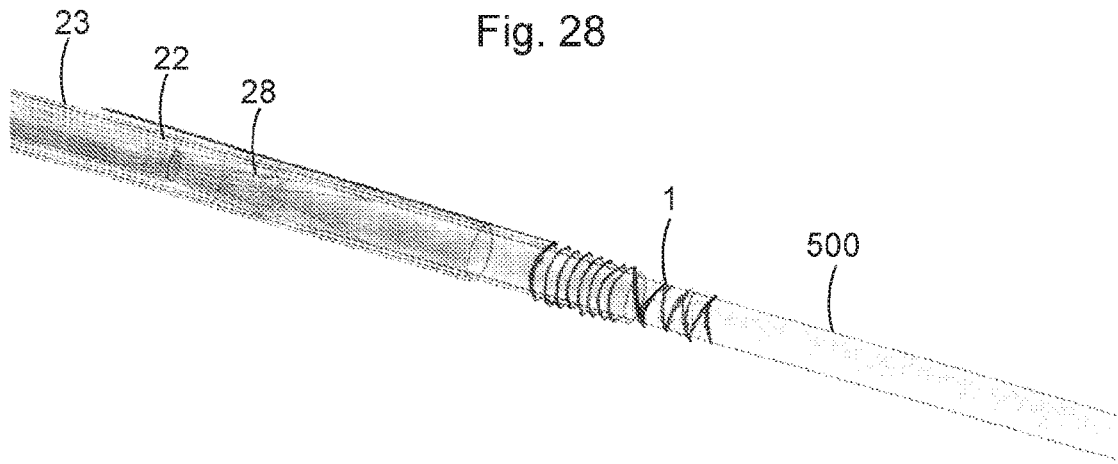
Figure 30:
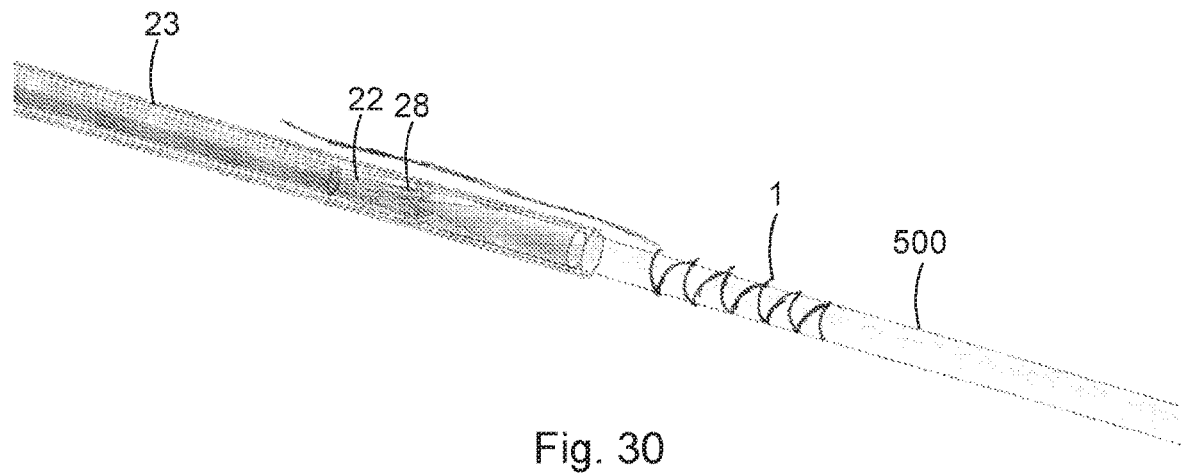
Figure 31:
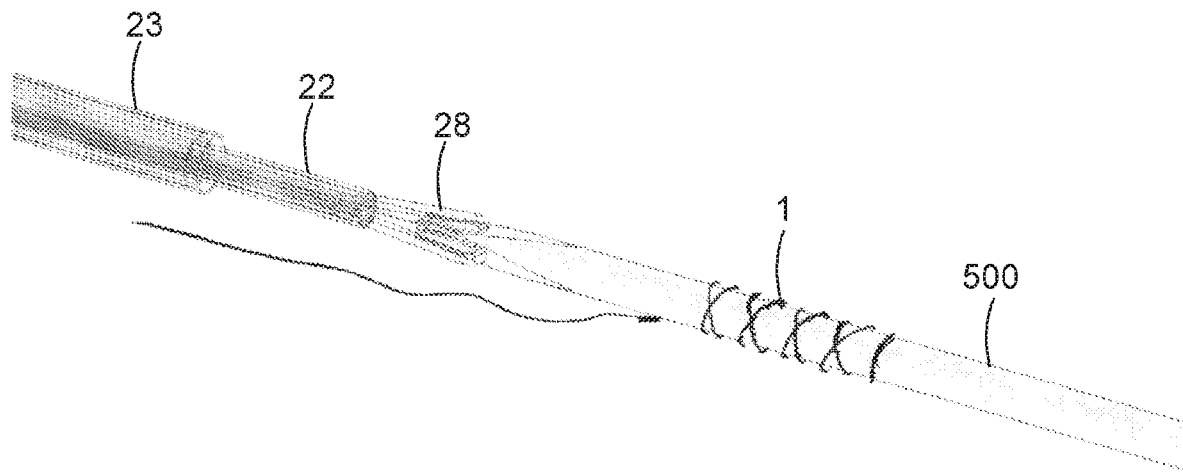
Figure 32:
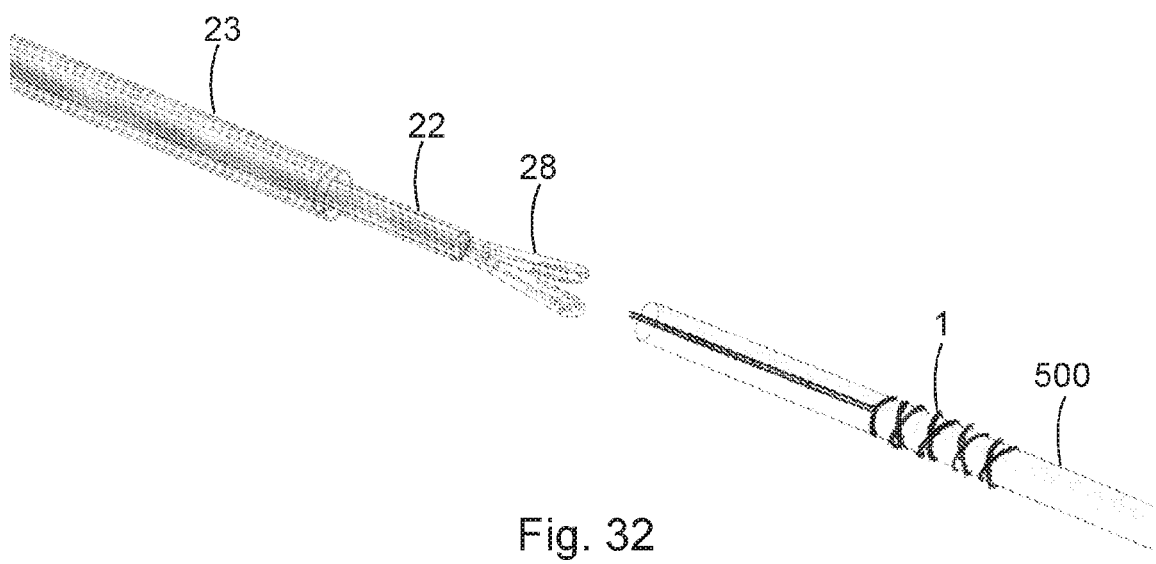

FIG. 22 illustrates an applicator 100 with a tendon grasping device 1 in a position where the gripper 28 is adjacent to an end of a tendon 500 stump. As seen in FIG. 23, and FIG. 24, which is a closeup view of FIG. 23, focusing on the gripper 28, the gripper 28 is actuated and grips the end of the tendon 500 stump. In FIG. 25, the inner stem 22 is inserted into the hollow sleeve 23, thus causing the end of the tendon 500 stump, gripped by the gripper 28, to enter into the hollow sleeve 23. In FIG. 26, and FIGS. 27-28, which are close up views of FIG. 26, focusing on the gripper 28, the tendon grasping device 1 is pushed towards the tendon 500 stump in a manner that the tendon grasping device 1 is applied over the tendon 500 stump, namely the tendon 500 stump is inserted into a hollow space defined by the tendon grasping device 1. In FIG. 29 the inner stem 22 is moved into the hollow sleeve 23. At this stage, a part of the tendon grasping device 1 for example the first end 18 of the tendon grasping device 1, is tightened over the tendon 500 stump. According to one embodiment, when the first part 18 of the tendon grasping device 1 is elastic, the first part 18 is naturally tightened over the tendon 500 stump. According to another embodiment, when the first part 18 of the tendon grasping device 1 is loose, the first part 18 is tightened over the tendon 500 stump either manually or by using a device. In FIG. 30, the entire tendon grasping device 1 is tightened over the tendon 500 stump. In the next stage, shown in FIG. 31, the gripper 28, while gripping the tendon 500 stump, is moved outside of the hollow sleeve 23, while the entire tendon grasping device 1 is tightened over the tendon 500 stump. This is followed by the stage shown in FIG. 32—release of the tendon 500 stump from the gripper 28 by bringing the gripper 28 to an open state. The result of this process is a tendon grasping device 1 tightened over a tendon 500 stump.

Figure 33:
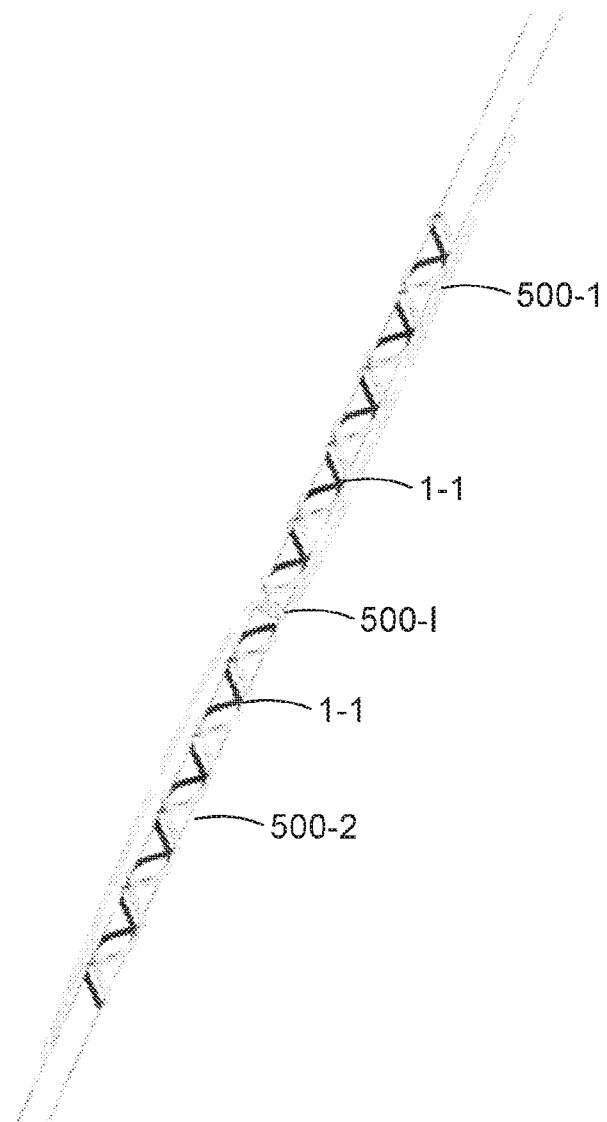
FIG. 33 schematically illustrates, according to an exemplary embodiment, a side perspective view of two tendon stumps joined using two tendon grasping device.

FIG. 33 schematically illustrates, according to an exemplary embodiment, a side perspective view of two tendon 500 stumps joined using two tendon grasping devices 1. A first tendon grasping device 1-1 is tightened over a first tendon 500-1 stump, and a second tendon grasping device 1-2 is tightened over a second tendon 500-2 stump. Thus, an end of the first tendon 500-1 stump is brought to proximity with an end of the second tendon 500-2 stump at point 500-1, by connecting the first tendon grasping devices 1-1 with the second tendon grasping device 1.

Figure 34A:
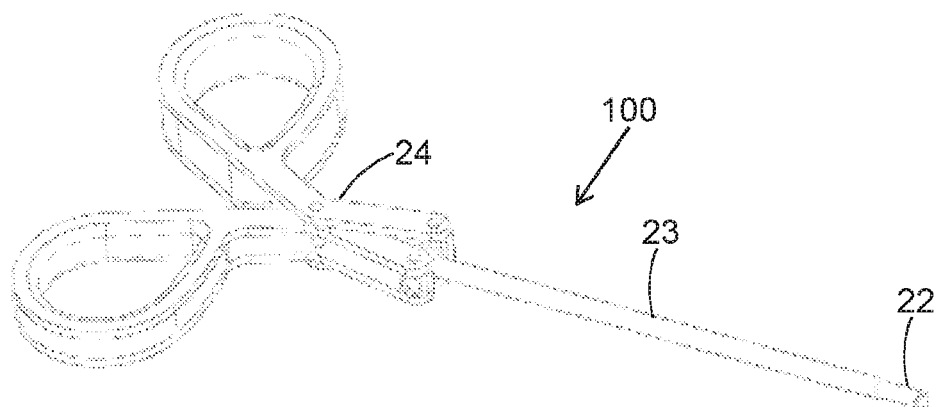
FIGS. 34A-C schematically illustrate, a side perspective view of additional embodiments of at least one handle of an applicator 100.
Figure 34B:
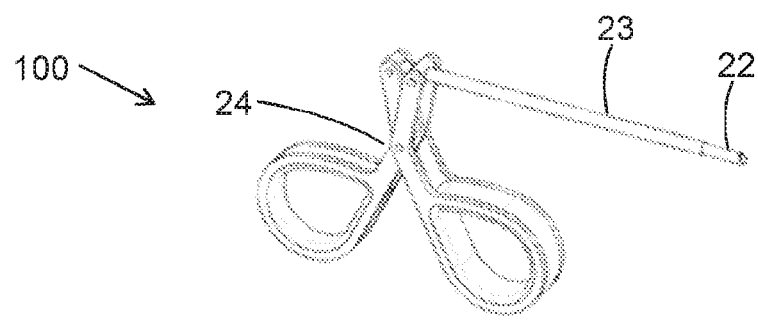
Figure 34C:
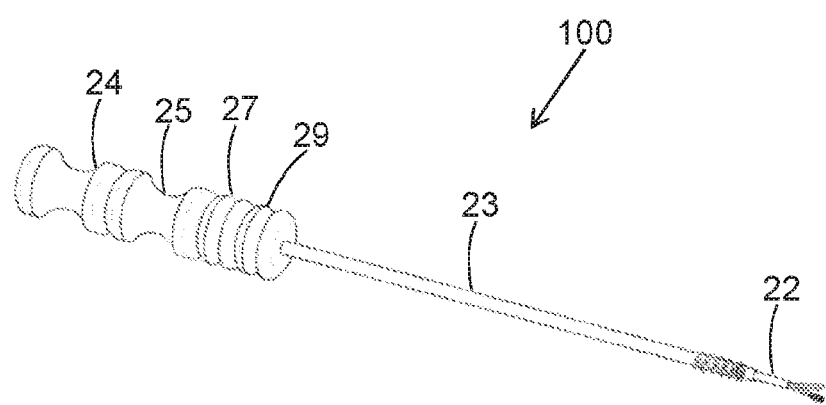

FIGS. 34A-C schematically illustrate, a side perspective view of additional embodiments of at least one handle of an applicator 100. According to one embodiment, illustrated in FIGS. 34A-B, the handle 24 is a scissors-like element facilitating control of the applicator 100, for example, moving of the hollow sleeve 23 and the inner stem 22 one relative to another, actuating the gripper 28, and the like. According to one embodiment, illustrated in FIG. 34A, the handle 24 in the form of a scissors-like element is horizontally attached to the hollow sleeve 23 and inner stem 22. According to another embodiment, illustrated in FIG. 34B, the handle 24 in the form of a scissors-like element is vertically attached to the hollow sleeve 23 and inner stem 22. According to the embodiment illustrated in FIGS. 34A-C, the applicator 100 comprises at least one handle, for example four handles, that are configured to be held by a user's hand, thus enabling controlling the applicator 100.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A set of two tendon grasping devices, whereby each one of the two tendon grasping devices is made of a biocompatible material that is suitable for surgery, comprising a series of curved elements being connected sequentially to form a hollow deformable structure, whereby in use each curved element of the series of curved elements is configured to surround a tendon and the structure deforms between a radially extended condition and a radially retracted condition, in which each curved element firmly is configured to surrounds the tendon and applies pressure around the tendon without penetrating the tendon, whereby the series of curved elements includes at least an end loop as well as a further loop connected to the end loop or a coil connected to the end loop, and whereby at least one of the tendon grasping devices further comprises attachment means to attach the tendon grasping device to the other tendon grasping device, said attachment means comprising at least one or more of the following: structure thread, clip, resilient ratchet element.

2. The set of two tendon grasping devices of claim 1, wherein said at least one tendon grasping device comprises a continuous linear element with portions of the linear element being connected at connecting points to from a series of sequentially flexibly connected loops.

3. The set of two tendon grasping devices of claim 1, wherein said set includes at least two tendon grasping devices that have different dimensions further comprising a tendon cover deployable from said device body prior to or following deployment of said at least one tendon-attachable element.

4. The set of two tendon grasping devices of claim 1, wherein said linear element is a thread or a ring.

5. The set of two tendon grasping devices of claim 1, wherein said at least one tendon grasping device is made at least partially from bio-degradable material.

6. The set of two tendon grasping devices of claim 1, wherein said at least one tendon grasping device is made at least partially from one of the following materials: Nitinol, suture strings, bio-compatible fibers or any combination thereof.

7. The set of two tendon grasping devices of claim 1, wherein said at least one tendon grasping device comprises a series of loops, wherein said each loop in the series of loops is formed by a discrete ring and wherein said each ring is flexibly connected with either one or maximum two other rings at connecting points.

8. The set of two tendon grasping devices device of claim 2, wherein said connection of the portions of the linear element at the connecting points is effected by one of the following: intercrossing the linear portions, knots, discrete connectors grasper includes a pair of movable jaws.

9. The set of two tendon grasping devices of claim 1, wherein said structure of said at least one tendon device includes two sequentially connected loops.

10. The set of two tendon grasping devices of claim 1, wherein said at least one tendon grasping device is attached to a further structure that has at least one loop that is made from a different material than the material of the structure that is retracted to the radially condition by resilient forces.

* * * * *